(12) United States Patent
Dörwald

(10) Patent No.: US 8,486,892 B2
(45) Date of Patent: Jul. 16, 2013

(54) BLOOD COAGULATION FACTOR INHIBITORS

(75) Inventor: Florencio Zaragoza Dörwald, Visp (CH)

(73) Assignee: Novo Nordisk Health Care AG, Zurich (CH)

( * ) Notice: Subject to any disclaimer, the term of this patent is extended or adjusted under 35 U.S.C. 154(b) by 233 days.

(21) Appl. No.: 12/811,854

(22) PCT Filed: Jan. 22, 2009

(86) PCT No.: PCT/EP2009/050709
§ 371 (c)(1),
(2), (4) Date: Sep. 7, 2010

(87) PCT Pub. No.: WO2009/092758
PCT Pub. Date: Jul. 30, 2009

(65) Prior Publication Data
US 2011/0003752 A1    Jan. 6, 2011

Related U.S. Application Data

(60) Provisional application No. 61/024,267, filed on Jan. 29, 2008.

(30) Foreign Application Priority Data

Jan. 23, 2008  (EP) .................................... 08100813

(51) Int. Cl.
*A61K 38/36*  (2006.01)
*A61K 38/08*  (2006.01)
*C07K 7/06*   (2006.01)
*A61P 7/02*   (2006.01)

(52) U.S. Cl.
USPC ........... 514/14.3; 530/328; 530/329; 530/330

(58) Field of Classification Search
None
See application file for complete search history.

(56) References Cited

FOREIGN PATENT DOCUMENTS

| EP | 1364960 | 11/2003 |
|----|---------|---------|
| WO | WO 89/09612 | 10/1989 |
| WO | WO 00/15658 | 3/2000 |
| WO | WO 2005/016365 | 2/2005 |
| WO | 2006/005667 A2 | 1/2006 |
| WO | 2006/089954 A2 | 8/2006 |
| WO | WO 2006/089952 | 8/2006 |
| WO | WO 2008/107362 | 9/2008 |
| WO | WO 2009/024571 | 2/2009 |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-497.*
Bradley et al., Limits of Cooperativity in a Structurally Modular Protein: Response of the Notch Ankyrin Domain to Analogous Alanine Substitut~ons in Each Repeat, J. Mol. BIoL (2002) 324, 373-386.*
Definition of derivative, from http://cancerweb.ncl.ac.uk/cgi-bin/omd?query=detivative, pp. 1-5. Accessed Jul. 7, 2005.*
Muller, Prodrug Approaches for Enhancing the Bioavailability of Drugs eith Low Solubility, Chemistry & Biodiversity, 2009, 6, pp. 2071-2083.*
Beaumont, et, al, Design of Ester Prodrugs to Enhance Oral Absorption of Poorly Permeable Compounds: Challenges to the Discovery Scientist, Current Drug Metabolism, 2003, 4, 461-485.*
Hyo-Kyung Han, Targeted Prodrug Design to Optimize Drug Delivery, AAPS Pharmsci 2000; 2 (1) article 6 pp. 1-11.*
Yashveer Singh et al, Recent Trends in Targeted Anticancer Prodrug and Conjugate Design, Curr Med Chem. 2008 ; 15(18): 1802-1826.*
Testa B., Prodrug Research: Futile or Fertile?, Biochem. Pharm., 2004, 68, pp. 2097-2106.*
Ettmayer, P. et al, Lessons Learned from Marketed and Investigational Prodrugs,J. Med. Chem., 2004, 47 (10), pp. 2393-2404.*
Nakase, Hiroshi et al. Bioscience Biotechnology Biochemistry Substrate Recognition Mechanism of Carboxypeptidase Y 2001 65 11 2465-2471.
Manning, M.C. et al., "Stability of Protein Pharmaceuticals", Pharmaceutical Research, vol. 6, No. 11, 1989, pp. 903-918.

* cited by examiner

*Primary Examiner* — Julie Ha
*Assistant Examiner* — Li Ni Komatsu
(74) *Attorney, Agent, or Firm* — Jianjie Hu

(57) ABSTRACT

The invention relates to novel compounds with formula (I) $X^1-X^2-X^3-X^4-X^5-(X^6)_n-(X^7)_m-Y$ useful as blood coagulation factor inhibitors. The compounds (I) may be used for treatment of thrombotic conditions or as stabilizers of liquid formulations of blood coagulation factors, in particular liquid formulations of FVIIa, Factor VII variants, or Factor VII derivatives.

34 Claims, No Drawings

BLOOD COAGULATION FACTOR INHIBITORS

CROSS-REFERENCE TO RELATED APPLICATIONS

This application is a 35 U.S.C. §371 national stage application of International Patent Application PCT/EP2009/050709 (published as WO 2009/092758 A1), filed Jan. 22, 2009, which claimed priority of European Patent Application 08100813.8, filed Jan. 23, 2008; this application further claims priority under 35 U.S.C. §119 of U.S. Provisional Application 61/024,267, filed Jan. 29, 2008.

FIELD OF THE INVENTION

The present invention relates to new inhibitors of the proteases involved in the blood coagulation cascade, to methods for their preparation, and to use of said inhibitors as stabilizers of blood coagulation factors such as serine proteases and vitamin K-dependent polypeptides, as additives or formulation-aids for blood coagulation factors. In particular, the invention relates to stabilizing Factor VIIa or other Factor VII polypeptides against chemical and/or physical degradation, particularly in aqueous liquid compositions thereof.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Jun. 2, 2010. The Sequence Listing is made up of 43 bytes, and the information contained in the attached "SEQUENCE LISTING" is identical to the information in the specification as originally filed. No new matter is added.

BACKGROUND OF THE INVENTION

The serine protease Factor VII (FVII) is one of the plasma glycoproteins involved in the blood coagulation process. FVII is mainly present in plasma as single-chain zymogen, and is cleaved by another protease (FXa) to give its two-chain, activated form, Factor VIIa (FVIIa).

The tissue factor/factor VIIa (TF/FVIIa) complex is the main trigger of thrombotic events. This complex is part of the extrinsic pathway of blood coagulation and mediates the activation of factors IX and X, ultimately leading to the generation of thrombin.

Factor VIIa has proven to be a valuable therapeutic agent for the treatment of haemophilia and bleeding. It is desirable to have administration forms of Factor VIIa suitable for both storage and for delivery. Ideally, the drug product is stored and administered as a liquid. Alternatively, the drug product is lyophilized, i.e. freeze-dried, and then reconstituted by adding a suitable diluent prior to patient use. It is desirable that the drug product has sufficient stability to enable long-term storage, e.g. for more than six months.

The decision whether to maintain the finished drug product as a liquid or to freeze-dry it is usually made on the basis of the stability of the protein drug in those forms. Protein stability can be affected, inter alia, by such factors as ionic strength, pH, temperature, repeated cycles of freeze/thaw, and exposure to shear forces. Active protein may be lost as a result of physical instabilities, e.g. via denaturation and/or aggregation (both soluble and insoluble aggregate formation), as well as chemical instabilities, including, for example, instability towards hydrolysis, deamidation and/or oxidation, to name just a few. Moreover, in the case of Factor VIIa, which is a serine protease, fragmentation due to autocatalysis may occur (autoproteolysis; enzymatic, self-catalyzed degradation). For a general review of the stability of protein pharmaceuticals, see, for example, Manning, et al., Pharmaceutical Research 6:903-918 (1989).

While the possible occurrence of protein instabilities is widely appreciated, it is generally very difficult to predict particular instability problems for a particular protein. Any of these instabilities can result in the formation of a protein by-product, or derivative, having reduced activity, increased toxicity and/or increased immunogenicity. Indeed, protein precipitation may lead to thrombosis, non-homogeneity of dosage form and amount, as well as clogged syringes. Furthermore, post-translational modifications such as, for example, gamma carboxylation of certain glutamic acid residues in the N-terminus and addition of carbohydrate side chains provide potential sites that may be susceptible to modification upon storage.

Thus, the safety and efficacy of any composition of a protein is directly related to its stability. Maintaining stability in a liquid form is generally a different task than maintaining stability in a lyophilized form because of highly increased potential for molecular motion and thereby increased probability of molecular interactions. Maintaining stability in a concentrated form is also a different task than the above, because of the propensity for aggregate formation at increased protein concentrations. Factor VIIa undergoes degradation by several pathways, especially aggregation (dimerisation/oligomerisation), oxidation and autolytic cleavage (clipping of the peptide backbone or "heavy chain degradation"). Furthermore, precipitation may occur.

Many of these processes can be slowed significantly by removal of water from the protein. However, the development of an aqueous composition for Factor VIIa has the advantages of eliminating reconstitution errors, thereby increasing dosing accuracy, as well as simplifying the use of the product clinically, thereby increasing patient compliance. Ideally, compositions of Factor VIIa should be stable for more than 6 months over a wide range of protein concentrations. This allows for flexibility in methods of administration. Generally, more highly concentrated forms allow for the administration of lower volumes, which is highly desirable from the patients' point of view. Liquid compositions can have many advantages over freeze-dried products with regard to ease of administration and use.

When developing a liquid composition, many factors are taken into consideration. Short-term, i.e. less than six months, liquid stability generally depends on avoiding gross structural changes, such as denaturation and aggregation. These processes are described in the literature for a number of proteins, and many examples of stabilizing agents exist. It is well-known that an agent effective in stabilizing one protein actually acts to destabilize another. Once the protein has been stabilized against gross structural changes, developing a liquid composition for long-term stability (e.g., greater than six months) depends on further stabilizing the protein from types of degradation specific to that protein. More specific types of degradation may include, for example, disulfide bond scrambling, oxidation of certain residues, deamidation, and/or cyclization. Although it is not always possible to pinpoint the individual degradation species, assays are developed to monitor subtle changes so as to monitor the ability of specific excipients to uniquely stabilize the protein of interest.

Today, the only commercially available, recombinantly produced FVII polypeptide composition is a freeze-dried Factor FVIIa product which is reconstituted before use; it contains a relatively low Factor VIIa concentration, e.g., about 0.6 mg/mL. A vial (1.2 mg) of NOVOSEVEN® (Novo Nordisk A/S, Denmark) contains 1.2 mg recombinant human Factor VIIa (rhFVIIA), 5.84 mg NaCl, 2.94 mg $CaCl_2H_2O$, 2.64 mg glycylglycine (GlyGly), 0.14 mg polysorbate 80, and 60.0 mg mannitol; it is reconstituted to pH 5.5 by addition of 2.0 mL water for injection (WFI). When reconstituted, the protein solution is stable for use for 24 hours at room temperature. Thus, no liquid, ready-for-use or concentrated Factor VII products are currently commercially available.

Liquid formulations of Factor VII polypeptides containing Factor VII inhibitors/stabilizers have previously been described. WO 2005016365 describes liquid, aqueous pharmaceutical compositions comprising a Factor VII polypeptide, a buffering agent, and at least one stabilising agent (iii) comprising a —C(=N—Z1-R1)-NH—Z2-R2 motif, e.g. benzamidine compounds and guanidine compounds such as arginine.

Accordingly, it is highly desirable, and an object of the present invention, to develop agents that inhibit degradation of FVII polypeptides in liquid (particularly aqueous liquid) or solid administration forms. It is particularly desirable to be able to provide an aqueous liquid pharmaceutical composition of a Factor VII polypeptide which provides acceptable control of chemical and/or physical degradation processes such as those outlined above. Accordingly, it is also an object of the present invention to develop agents that, besides inhibiting or decreasing enzymatic activity of activated Factor VII polypeptides, are (i) reversible in their inhibitory action, (ii) sufficiently potent to require only minor concentrations present in the final product, (iii) non-toxic at the level present, and (iv) sufficiently soluble in aqueous medium at physiological conditions to allow for a substantial inhibition of the Factor VII polypeptide present.

SUMMARY OF THE INVENTION

The present invention provides compounds of formula (I)

$$X^1\text{-}X^2\text{-}X^3\text{-}X^4\text{-}X^5\text{-}(X^6)_n\text{-}(X^7)_m\text{-}Y \qquad (I)$$

wherein, $X^1$ represents lower alkoxycarbonyl, lower alkenyloxycarbonyl, alkynyloxycarbonyl, cycloalkyloxycarbonyl, cycloalkylalkyloxycarbonyl, aryloxycarbonyl, arylalkyloxycarbonyl, or heteroarylalkyloxycarbonyl, lower alkylaminocarbonyl, lower alkenylaminocarbonyl, alkynylaminocarbonyl, cycloalkylaminocarbonyl, cycloalkylalkylaminocarbonyl, arylaminocarbonyl, arylalkylaminocarbonyl, or heteroarylalkylaminocarbonyl, lower alkanoyl, lower alkenoyl, lower alkadienyl, alkynoyl, cycloalkanoyl, cycloalkylalkanoyl, cycloalkenylalkanoyl, aroyl, arylalkanoyl, or heteroarylalkanoyl, wherein said groups are optionally substituted with halogen, hydroxyl, lower alkyl, lower alkoxy, lower alkylthio, or cyano; $X^2$ represents 4-amidino-Phe, Arg, HomoArg, Orn, Lys, Dab, or Dap; $X^3$ represents Glu, Asp, (α-Me)Glu, 1-aminocyclobutane-trans-1,3-dicarboxylic acid, or 1-aminocyclobutane-cis-1,3-dicarboxylic acid; $X^4$ represents Arg, HomoArg, Lys, His, Asn, Gln, Trp, Phe, Phg, Glu, D-Glu, Asp, D-Asp, Dab, Dap, Nβ-[amidino]-Dap, or Nγ-[amidino]Dab; $X^5$ represents Phg, D-Phg, Phe, Val, Ile, Leu, Lys, Ala, Glu, Gly, Aib, Trp, Abu, Alle, Cha, Hph, Nle, or Nva; $X^6$ represents Arg, HomoArg, Lys, His, Orn, or Lys(mPeg(1-10k)-CO); $X^7$ represents a diradical of general formula —HN—($CH_2$—$CH_2$—O)$_{1\text{-}10}$—($CH_2$)$_{1\text{-}5}$—C(=O)—; Y represents $NH_2$ or OH; and n is 0 or 3-6 and m is 0-20, with the proviso that n and m must not be zero simultaneously, including any and all stereoisomeric form or forms thereof, any mixture of two or more such compounds of formula I in any ratio, and physiologically tolerable salts and prodrugs thereof.

The present inventors have discovered that compounds of general formula (I) are inhibitors of the proteases involved in the blood coagulation cascade, and may therefore be used as stabilizing additives for formulations of Factor VII polypeptides, particularly aqueous solutions of FVIIa. Blood coagulation Factor VII, or analogues or derivatives thereof ("Factor VII polypeptides"), when formulated as liquid aqueous pharmaceutical compositions together with at least one stabilising agent according to formula (I), exhibit improved stability and thereby allow for prolonged storage before and/or during actual use.

The present invention further provides: (i) processes for the preparation of compounds of formula (I); (ii) pharmaceutical compositions comprising a FVII polypeptide, such as wild-type FVIIa, rhFVIIa, or analogues or derivatives thereof, and a compound of formula (I); (iii) methods for preparing a pharmaceutical compositions comprising a FVII polypeptide, such as wild-type FVIIa, rhFVIIa, or analogues thereof, and a compound of formula (I); (iv) methods for inhibiting a FVII polypeptide, such as wild-type FVIIa, rhFVIIa, or analogues or derivatives thereof; (v) the use of compounds of formula (I), in combination with a FVII polypeptide, such as wild-type FVIIa, rhFVIIa, or analogues or derivatives thereof, for the manufacture of pharmaceutical compositions for the treatment of bleeding, haemophilia, or other diseases or symptoms, in which the treatment with a FVII polypeptide is beneficial.

DETAILED DESCRIPTION OF THE INVENTION

As mentioned above, the present invention provides novel compounds with formula (I) (see above) that inhibit degradation of serine proteases, such as e.g. Factor VII polypeptides in liquid (particularly aqueous liquid) or solid administration forms. Furthermore, the invention provides aqueous liquid pharmaceutical compositions of serine proteases, in particular Factor VII polypeptides, which provide acceptable control of chemical and/or physical degradation processes such as those outlined above. Factor VII or analogues thereof ("Factor VII polypeptides"), when formulated as liquid, aqueous pharmaceutical compositions together with at least one compound with formula (I) exhibits improved stability and thereby allow for prolonged (e.g. 6 months or more) storage before actual use.

Compounds of formula (I) are capable of reversibly inhibiting Factor VIIa and may be employed as stabilizers in formulations or compositions, notable aqueous formulations or compositions, comprising a Factor VII polypeptide (see below). In this connection, compounds of the invention frequently exhibit favourable solubility in water or other aqueous media.

In the present context, the term "alkyl" is intended to indicate a straight or branched saturated monovalent hydrocarbon radical. The term "alkylene" indicates the corresponding diradical. A "lower alkyl" is an alkyl having from 1 to 6 carbon atoms, also denoted as C1-6-alkyl. C1-6-alkyl groups include for instance methyl, ethyl, n-propyl, isopropyl, n-butyl, sec-butyl, isobutyl, tert-butyl, n-pentyl, 2-methylbutyl, 3-methylbutyl, 4-methylpentyl, n-hexyl, 1,1-dimethylpropyl, 1,2-dimethylpropyl, 2,2-dimethylpropyl (neopentyl) and 1,2,2-trimethylpropyl.

The term "alkoxy" is intended to indicate a radical wherein an alkyl group in either a linear or branched or cyclic configuration is linked through an ether oxygen and having its free valence bond from the ether oxygen (alkyl-O—). A "lower alkoxy" is an alkoxy radical wherein the alkyl group has from 1 to 6 carbon atoms, also denoted as C1-6-alkoxy. Examples of linear alkoxy groups are methoxy, ethoxy, propoxy, butoxy, pentoxy and hexoxy. Examples of branched alkoxy include isopropoxy, sec-butoxy, tert-butoxy, isopentoxy and isohexoxy. Examples of cyclic alkoxy include cyclopropyloxy, cyclobutyloxy, cyclopentyloxy and cyclohexyloxy.

The term "alkoxycarbonyl" is intended to indicate a monovalent substituent comprising an alkoxy group linked, via the ether oxygen, through a carbonyl group (alkyl-O—C(=O)—); such as e.g. methoxycarbonyl, carbethoxy, propoxycarbonyl, isopropoxycarbonyl, n-butoxycarbonyl, sec-butoxycarbonyl, tert-butoxycarbonyl, 3-methylbutoxycarbonyl, n-hexoxycarbonyl and the like. A "lower alkoxycarbonyl" is an alkoxycarbonyl radical wherein the alkyl group has from 1 to 6 carbon atoms, also denoted as C1-6-alkoxycarbonyl.

The term "alkenyl" is intended to indicate an olefinically unsaturated branched or straight group having from 2 to the 15 number of carbon atoms and at least one double bond. Examples of such groups include, but are not limited to, vinyl, 1-propenyl, 2-propenyl, allyl, iso-proppenyl, 1,3-butadienyl, 1-butenyl, hexenyl, pentenyl, and the like.

The term "alkanoyl" as used herein is intended to indicate straight and branched chain alkanoyl groups of one to twenty carbons.

The term "alkenoyl" as used herein is intended to indicate straight and branched chain alkenoyl groups of one to twenty carbons containing at least one carbon-carbon double bond.

The term "alkadienyl", is intended to indicate a straight-chain or branched hydrocarbon residue comprising 2 olefinic bonds and up to 20 carbon atoms.

In the present context, the term "cycloalkyl" is intended to indicate a cyclic saturated monovalent hydrocarbon radical. A "lower cycloalkyl" is an cycloalkyl having from three to six carbon atoms, also denoted as C1-6-cycloalkyl. C1-6-cycloalkyl groups include for instance cyclopropyl, cyclobutyl, cyclopentyl, 2-methyl-cyclopentyl, and cyclohexyl.

The term 'amidino' refers to —C(=NH)NH$_2$, the term 'guanidino' refers to —NH—C(=NH)NH$_2$.

The term "aryl" as used herein is intended to indicate a mono- or polycyclic carbocyclic aromatic ring radical with for instance 6 to 10 member atoms, or an aromatic ring system radical with for instance from 10 to 22 member atoms. Aryl is also intended to include the partially hydrogenated derivatives of the carbocyclic systems, wherein at least one ring is aromatic. Examples of such partially hydrogenated derivatives include 1,2,3,4-tetrahydronaphthyl, fluorenyl and 1,4-dihydronaphthyl.

The term "heteroaryl" as used herein is intended to indicate a mono- or polycyclic heterocyclic aromatic ring radical with for instance 5 to 13 member atoms, or a heterocyclic aromatic ring system radical with for instance from 13 to 21 member atoms, containing one or more heteroatoms selected from nitrogen, oxygen, and sulfur, wherein N-oxides and sulfur monoxides and sulfur dioxides are permissible heteroaromatic substitutions, such as for instance furyl, thienyl, thiophenyl, pyrrolyl, oxazolyl, thiazolyl, imidazolyl, pyrazolyl isoxazolyl, oxadiazoly, thiadiazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, indazolyl, benzimidazolyl, benzthiazolyl, benzisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like. Heteroaryl is also intended to include the partially hydrogenated derivatives of the heterocyclic systems, provided at least one ring comprising a hetero atom is aromatic. Examples of such partially hydrogenated derivatives include 2,3-dihydrobenzofuranyl, pyrrolinyl, pyrazolinyl, indolinyl, oxazolidinyl, oxazolinyl and oxazepinyl.

Examples of "aryl" and "heteroaryl" include, but are not limited to phenyl, biphenylyl, indenyl, fluorenyl, phenanthrenyl, azulenyl, naphthyl (1-naphthyl, 2-naphthyl), anthracenyl (1-anthracenyl, 2-anthracenyl, 3-anthracenyl), thienyl (2-thienyl, 3-thienyl), furyl (2-furyl, 3-furyl), indolyl, oxadiazolyl, isoxazolyl, thiadiazolyl, oxatriazolyl, thiatriazolyl, quinazolin, fluorenyl, xanthenyl, isoindanyl, benzhydryl, acridinyl, thiazolyl, pyrrolyl (1-pyrrolyl, 2-pyrrolyl, 3-pyrrolyl), pyrazolyl (1-pyrazolyl, 3-pyrazolyl, 4-pyrazolyl, 5-pyrazolyl), imidazolyl (1-imidazolyl, 2-imidazolyl, 4-imidazolyl, 5-imidazolyl), triazolyl (1,2,3-triazol-1-yl, 1,2,3-triazol-4-yl 1,2,3-triazol-5-yl, 1,2,4-triazol-3-yl, 1,2,4-triazol-5-yl), oxazolyl (2-oxazolyl, 4-oxazolyl, 5-oxazolyl), isooxazolyl (isooxazo-3-yl, isooxazo-4-yl, isooxaz-5-yl), isothiazolyl (isothiazo-3-yl, isothiazo-4-yl, isothiaz-5-yl)thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydrobenzo[b]furanyl (2-(2,3-dihydrobenzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydrobenzo[b]furanyl)), benzo[b]thiophenyl (benzo[b]thiophen-2-yl, benzo[b]thiophen-3-yl, benzo[b]thiophen-4-yl, benzo[b]thiophen-5-yl, benzo[b]thiophen-6-yl, benzo[b]thiophen-7-yl), 2,3-dihydro-benzo[b]thiophenyl (2,3-dihydro-benzo[b]thiophen-2-yl, 2,3-dihydro-benzo[b]thiophen-3-yl, 2,3-dihydro-benzo[b]thiophen-4-yl, 2,3-dihydro-benzo[b]thiophen-5-yl, 2,3-dihydro-benzo[b]thiophen-6-yl, 2,3-dihydrobenzo[b]thiophen-7-yl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (2-benzoxazolyl, 3-benzoxazolyl, 4-benzoxazolyl, 5-benzoxazolyl, 6-benzoxazolyl, 7-benzoxazolyl), benzothiazolyl (2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), benzo[1,3]dioxole (2-benzo[1,3]dioxole, 4-benzo[1,3]dioxole, 5-benzo[1,3]dioxole, 6-benzo[1,3]dioxole, 7-benzo[1,3]dioxole), and tetrazolyl (5-tetrazolyl, N-tetrazolyl).

The term "Lys(mPeg(1-10k)-CO)" as used herein is intended to indicate a lysine which is acylated at the side-chain amino group with a methoxy-poly(ethylene glycol) derived carboxylic acid (MeO—($CH_2$—$CH_2$—O)$_n$—($CH_2$)$_m$—$CO_2H$) of the molecular weight 1-10 kDa, m and n being variable integers. Typical values for n are 20-200, such as 20-100 or 50-150 or 80-120 or 120-200; typical values for m are 1-5. The compounds of formula (I) can be pegylated, e.g. with the use of Lys(mPeg(1-10k)-CO). Pegylation of the compounds of formula (I) can improve the solubility of FVII. When FVII is bound to the pegylated compounds of formula (I), the Peg-chain should reduce interactions between the protein molecules, and thus prevent them from aggregating and precipitating.

As used herein, the term "prodrug" includes biohydrolyzable amides and biohydrolyzable esters, acetals, aminals, carbamates, thioaminals, thioacetals, and hydrazones, and also encompasses a) compounds in which the biohydrolyzable functionality in such a prodrug is encompassed in the compound according to the present invention, and b) compounds which may be oxidized or reduced biologically at a given functional group to yield drug substances according to the present invention. Examples of these functional groups include 1,4-dihydropyridine, N-alkylcarbonyl-1,4-dihydropyridine, 1,4-cyclohexadiene, tert-butyl, and the like. The invention also comprises prodrugs of compounds of formula (I).

Stereogenic atoms present in the compounds of formula (I) can independently of each other have R configuration or S configuration. The compounds of formula (I) can be pure enantiomers or mixtures of enantiomers, e.g. racemates, or pure diastereomers or mixtures of diastereomers. The invention also comprises all tautomeric forms of compounds of formula (I).

In the present context, the term "pharmaceutically tolerable salt" is intended to indicate salts which are not harmful to the patient. Such salts include pharmaceutically tolerable acid addition salts, pharmaceutically tolerable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically tolerable inorpanic or organic acid addition salts include the pharmaceutically tolerable salts listed in J. Pharm. Sci. 66, 2 (1977), which is incorporated herein by reference. Examples of metal salts include, without limitation, lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. The present invention also comprises pharmaceutically tolerable salts of compounds of formula (I).

As used herein, the term "solvate" is a complex of defined stoichiometry formed by a solute and a solvent. Solvents may be, by way of example, water, ethanol, or acetic acid.

In some embodiments, the invention relates to compounds of formula (I), wherein $X^1$ represents lower alkoxycarbonyl, lower alkenyloxycarbonyl, alkynyloxycarbonyl, cycloalkyloxycarbonyl, cycloalkylalkyloxycarbonyl, aryloxycarbonyl, arylalkyloxycarbonyl, or heteroarylalkyloxycarbonyl, lower alkylaminocarbonyl, lower alkenylaminocarbonyl, alkynylaminocarbonyl, cycloalkylaminocarbonyl, cycloalkylalkylaminocarbonyl, arylaminocarbonyl, arylalkylaminocarbonyl, or heteroarylalkylaminocarbonyl, lower alkanoyl, lower alkenoyl, lower alkadienyl, alkynoyl, cycloalkanoyl, cycloalkylalkanoyl, cycloalkenylalkanoyl, aroyl, arylalkanoyl, or heteroarylalkanoyl, wherein said groups are optionally substituted with halogen, hydroxyl, lower alkyl, lower alkoxy, lower alkylthio, or cyano. In other embodiments, $X^1$ represents lower alkoxycarbonyl, lower alkenyloxycarbonyl, alkynyloxycarbonyl, cycloalkyloxycarbonyl, cycloalkylalkyloxycarbonyl, lower alkylaminocarbonyl, lower alkenylaminocarbonyl, alkynylaminocarbonyl, cycloalkylaminocarbonyl, cycloalkylalkylaminocarbonyl, lower alkanoyl, lower alkenoyl, alkynoyl, cycloalkanoyl, or cycloalkylalkanoyl, and wherein said groups are optionally substituted with halogen, lower alkyl, lower alkoxy, or lower alkylthio. In yet another embodiment, $X^1$ represents methoxycarbonyl, ethoxycarbonyl, propyloxycarbonyl, 2-(methoxy)ethoxycarbonyl, 2-(methylthio)ethoxycarbonyl, isopropoxycarbonyl, allyloxycarbonyl, 2-chloroallyloxycarbonyl, propargyloxycarbonyl, isobutoxycarbonyl, cyclobutyloxycarbonyl, cyclopentyloxycarbonyl, cyclopropylmethyloxycarbonyl, methylaminocarbonyl, dimethylaminocarbonyl, ethylaminocarbonyl, diethylaminocarbonyl, propylaminocarbonyl, isopropylaminocarbonyl, allylaminocarbonyl, cyclobutylaminocarbonyl, cyclopentylaminocarbonyl, cyclopropylmethylaminocarbonyl, acetyl, propionyl, butyryl, pentanoyl, 3-cyclopropylpropionyl, pent-4-enoyl, 2-methyl-4-pentenoyl, 4-hexenoyl, 3-cyclopenten-1-oyl, 4,5,5-trifluoropent-4-enoyl, or hexa-2,4-dienoyl. In one embodiment, $X^1$ represents propyloxycarbonyl.

In some embodiments, the invention relates to compounds of formula (I), wherein $X^2$ represents 4-amidinoPhe, Arg, HomoArg, Orn, Lys, Dab, or Dap. In other embodiments, $X^2$ represents 4-amidinoPhe, Arg, HomoArg, Orn, or Lys. In yet another embodiment, $X^2$ represents 4-amidinoPhe.

In some embodiments, the invention relates to compounds of formula (I), wherein $X^3$ represents Glu, Asp, (α-Me)Glu, 1-aminocyclobutane-trans-1,3-dicarboxylic acid, or 1-aminocyclobutane-cis-1,3-dicarboxylic acid. In another embodiment, $X^3$ represents Glu.

In some embodiments, the invention relates to compounds of formula (I), wherein $X^4$ represents Arg, HomoArg, Lys, His, Asn, Gln, Trp, Phe, Phg, Glu, D-Glu, Asp, D-Asp, Dab, Dap, Nβ-[amidino]-Dap, or Nγ-[amidino]Dab. In other embodiments, $X^4$ represents Arg, HomoArg, Lys, His, Asn, Gln, Dab, or Dap. In yet further embodiments, $X^4$ represents Asn or Gln.

In some embodiments, the invention relates to compounds of formula (I), wherein $X^5$ represents Phg, D-Phg, Phe, Val, Ile, Leu, Lys, Ala, Glu, Gly, Aib, Trp, Abu, Alle, Cha, Hph, Nle, or Nva. In other embodiments, $X^5$ represents Phe, Val, Ile, Leu, Ala, Cha, Gly, or Trp. In yet further embodiments, $X^5$ represents Phe, Cha, or Trp.

In some embodiments, the invention relates to compounds of formula (I), wherein $X^6$ represents Arg, HomoArg, Lys, His, Orn, or Lys(mPeg(1-10k)-CO). In other embodiments, $X^6$ represents His, Arg, HomoArg, or Orn. In yet another embodiment, $X^6$ represents Arg.

In some embodiments, the invention relates to compounds of formula (I), wherein
$X^7$ represents a diradical of general formula —HN—($CH_2$—$CH_2$—O)$_{1-10}$-($CH_2$)$_{1-5}$—C(=O)—. In yet further embodiments, $X^7$ represents —HN—($CH_2$—$CH_2$—O)$_2$—($CH_2$)—C(=O)— or —HN—($CH_2$—$CH_2$—O)$_2$—($CH_2$)$_3$—C(=O)—.

In one embodiment of the invention, Y represents $NH_2$, and in another embodiment OH.

In some embodiments, the invention relates to compounds of formula (I), wherein n is 0 or 3-6 and m is 0-20, with the proviso that n and m must not be zero simultaneously. In other embodiments, n is 3-6 and m is 0. In yet another embodiment, n is 3 and m is 0. In other embodiments, n is 0 and m is 1-20. In yet another embodiment, n is 0 and m is 5. In a still further embodiment, n is 0 and m is 10.

In a further embodiment, the compound with formula (I) is selected from the list of:
Propyloxycarbonyl-(4-amidino-Phe)-Glu-Asn-Cha-[HN—($CH_2$—$CH_2$—O)$_2$—($CH_2$)—C(=O)]$_5$—$NH_2$;
Propyloxycarbonyl-(4-amidino-Phe)-Glu-Asn-Cha-[HN—($CH_2$—$CH_2$—O)$_2$—($CH_2$)—C(=O)]$_{10}$—$NH_2$;
Propyloxycarbonyl-(4-amidino-Phe)-Glu-Asn-Cha-[Arg]$_3$—$NH_2$;
Propyloxycarbonyl-HomoArg-Glu-Asn-Cha-[HN—($CH_2$—$CH_2$—O)$_2$—($CH_2$)—C(=O)]$_5$—$NH_2$;
Propyloxycarbonyl-HomoArg-Glu-Asn-Cha-[HN—($CH_2$—$CH_2$—O)$_2$—($CH_2$)—C(=O)]$_{10}$—$NH_2$;
Propyloxycarbonyl-HomoArg-Glu-Asn-Cha-[Arg]$_3$—$NH_2$,
including any and all stereoisomeric form or forms thereof, any mixture of two or more such compounds of formula I in any ratio, and physiologically tolerable salts and prodrugs thereof.

The compounds of formula I are reversible inhibitors of Factor VII polypeptides (in their activated form). Preferably, they are specific inhibitors of Factor VII polypeptides. As used herein, the term specific when used in reference to the inhibition of Factor VIIa activity means that a compound of the formula I can inhibit Factor VII activity without substantially inhibiting the activity of other specified proteases involved in the blood coagulation and/or the fibrinolysis pathway including, for example, Factor Xa, plasmin, thrombin, Factor IXa, Factor XIa, Factor XIIa and tissue-plasminogen activator (tPA) (using the same concentration of the inhibitor).

The present specification describes assays and methods (see below) for determining the inhibition constant ($K_i$) for a Factor VII polypeptide as well as other specified proteases involved in the blood coagulation and/or the fibrinolysis pathway.

In preferred embodiments of the invention, the compounds of formula I exhibit one or more of the following:
a $K_i$ (activated Factor VII polypeptide) of 1/10 or less (such as 1/20 or less, 1/50 or less, 1/100 or less, 1/200 or less, 1/500 or less, from 1/2-1/10, from 1/10-1/20, from 1/10-1/50, from 1/20-1/100, from 1/50-1/200, from 1/100-1/500, from 1/100-1/1000, from 1/200-1/1000) of $K_i$ (Factor Xa) (using the same concentration of the inhibitor);
a $K_i$ (activated Factor VII polypeptide) of 1/10 or less (such as 1/20 or less, 1/50 or less, 1/100 or less, 1/200 or less, 1/500 or less, from 1/2-1/10, from 1/10-1/20, from 1/10-1/50, from 1/20-1/100, from 1/50-1/200, from 1/100-1/500, from 1/100-1/1000, from 1/200-1/1000) of $K_i$ (plasmin) (using the same concentration of the inhibitor);
a $K_i$ (activated Factor VII polypeptide) of 1/10 or less (such as 1/20 or less, 1/50 or less, 1/100 or less, 1/200 or less, 1/500 or less, from 1/2-1/10, from 1/10-1/20, from 1/10-1/50, from 1/20-1/100, from 1/50-1/200, from 1/100-1/500, from 1/100-1/1000, from 1/200-1/1000) of $K_i$ (thrombin) (using the same concentration of the inhibitor);
a $K_i$ (activated Factor VII polypeptide) of 1/10 or less (such as 1/20 or less, 1/50 or less, 1/100 or less, 1/200 or less, 1/500 or less, from 1/2-1/10, from 1/10-1/20, from 1/10-1/50, from 1/20-1/100, from 1/50-1/200, from 1/100-1/500, from 1/100-1/1000, from 1/200-1/1000) of $K_i$ (Factor IXa) (using the same concentration of the inhibitor);
a $K_i$ (activated Factor VII polypeptide) of 1/10 or less (such as 1/20 or less, 1/50 or less, 1/100 or less, 1/200 or less, 1/500 or less, from 1/2-1/10, from 1/10-1/20, from 1/10-1/50, from 1/20-1/100, from 1/50-1/200, from 1/100-1/500, from 1/100-1/1000, from 1/200-1/1000) of $K_i$ (Factor XIa) (using the same concentration of the inhibitor);
a $K_i$ (activated Factor VII polypeptide) of 1/10 or less (such as 1/20 or less, 1/50 or less, 1/100 or less, 1/200 or less, 1/500 or less, from 1/2-1/10, from 1/10-1/20, from 1/10-1/50, from 1/20-1/100, from 1/50-1/200, from 1/100-1/500, from 1/100-1/1000, from 1/200-1/1000) of $K_i$ (Factor XIIa) (using the same concentration of the inhibitor);
a $K_i$ (activated Factor VII polypeptide) of 1/10 or less (such as 1/20 or less, 1/50 or less, 1/100 or less, 1/200 or less, 1/500 or less, from 1/2-1/10, from 1/10-1/20, from 1/10-1/50, from 1/20-1/100, from 1/50-1/200, from 1/100-1/500, from 1/100-1/1000, from 1/200-1/1000) of $K_i$ (tPA) (using the same concentration of the inhibitor).

Factor VII Polypeptides

As used herein, the terms "Factor VII polypeptide" or "FVII polypeptide" means any protein comprising the amino acid sequence 1-406 of wild-type human Factor VIIa (i.e., a polypeptide having the amino acid sequence disclosed in U.S. Pat. No. 4,784,950), variants thereof as well as Factor VII-related polypeptides, Factor VII derivatives and Factor VII conjugates. This includes FVII variants, Factor VII-related polypeptides, Factor VII derivatives and Factor VII conjugates exhibiting substantially the same or improved biological activity relative to wild-type human Factor VIIa.

The term "Factor VII" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa. Such variants of Factor VII may exhibit different properties relative to human Factor VII, including stability, phospholipid binding, altered specific activity, and the like.

"Factor VII" or "Factor VIIa" within the above definition also includes natural allelic variations that may exist and occur from one individual to another. Also, degree and location of glycosylation or other post-translation modifications may vary depending on the chosen host cells and the nature of the host cellular environment.

As used herein, "wild type human FVIIa" is a polypeptide having the amino acid sequence disclosed in U.S. Pat. No. 4,784,950.

As used herein, "Factor VII-related polypeptides" encompasses polypeptides, including variants, in which the Factor VIIa biological activity has been substantially modified, such as reduced, relative to the activity of wild-type Factor VIIa. These polypeptides include, without limitation, Factor VII or Factor VIIa into which specific amino acid sequence alterations have been introduced that modify or disrupt the bioactivity of the polypeptide.

The term "Factor VII derivative" as used herein, is intended to designate a FVII polypeptide exhibiting substantially the same or improved biological activity relative to wild-type Factor VII, in which one or more of the amino acids of the parent peptide have been genetically and/or chemically and/ or enzymatically modified, e.g. by alkylation, glycosylation, PEGylation, acylation, ester formation or amide formation or the like. This includes but is not limited to PEGylated human Factor VIIa, cysteine-PEGylated human Factor VIIa and variants thereof. Non-limiting examples of Factor VII derivatives includes GlycoPegylated FVII derivatives as disclosed in WO 03/31464 and US Patent applications US 20040043446, US 20040063911, US 20040142856, US 20040137557, US 20040132640, WO2007022512, and US 20070105755 (Neose Technologies, Inc.); FVII conjugates as disclosed in WO 01/04287, US patent application 20030165996, WO 01/58935, WO 03/93465 (Maxygen ApS) and WO 02/02764, US patent application 20030211094 (University of Minnesota).

PEGylated human Factor VIIa encompasses any Factor VIIa to which one or more PEG moieties has been attached. The PEG molecule may be attached to any part of the Factor VIIa polypeptide, including any amino acid residue or carbohydrate moiety of the Factor VIIa polypeptide. The term "cysteine-PEGylated human Factor VIIa" refers to Factor VIIa having a PEG molecule conjugated to a sulfhydryl group of a cysteine introduced in human Factor VIIa to form a Factor VIIa sequence variant.

The term "PEGylated" is in terms of the present invention synonymous with the term "functionalised with a PEG moiety". The one or more PEG moieties which represent the functionalisation of the Factor VII polypeptide are covalently linked either to any part of the polypeptide backbone of the Factor VII polypeptide or to an oligosaccharide which is an integral part of the Factor VII polypeptide ("glycopegylated Factor VII polypeptide"). Glycopegylated Factor VII is thoroughly described in the applicant's earlier applications WO 2004/000366 A1 and WO 2005/014035 A1. This being said, the PEG moieties typically have a molecular weight of at least 300 Da, such as 300-100,000 Da; such as 5,000-50,000 Da; such as about 10,000 to about 45,000 Da; such as about 35,000 to about 45,000, or about 40.000 Da; or 500-20,000 Da, or 500-15,000 Da, or 2,000-15,000 Da, or 3,000-15,000 Da, or 3,000-12,000 Da, or about 10.000 Da. The PEG moieties may be linear or branched.

The term "improved biological activity" refers to FVII polypeptides with i) substantially the same or increased proteolytic activity compared to recombinant wild type human Factor VIIa or ii) to FVII polypeptides with substantially the same or increased TF binding activity compared to recombinant wild type human Factor VIIa or iii) to FVII polypeptides with substantially the same or increased half life in blood plasma compared to recombinant wild type human Factor VIIa.

Non-limiting examples of Factor VII variants having substantially the same or increased proteolytic activity compared to recombinant wild type human Factor VIIa include S52A-FVIIa, S60A-FVIIa (Lino et al., Arch. Biochem. Biophys. 352: 182-192, 1998); FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Kornfelt et al., Arch. Biochem. Biophys. 363:43-54, 1999); FVII variants as disclosed in PCT/DK02/00189 (corresponding to WO 02/077218); and FVII variants exhibiting increased proteolytic stability as disclosed in WO 02/38162 (Scripps Research Institute); FVII variants having a modified Gla-domain and exhibiting an enhanced membrane binding as disclosed in WO 99/20767, U.S. Pat. No. 6,017,882 and U.S. Pat. No. 6,747,003, US patent application 20030100506 (University of Minnesota) and WO 00/66753, US patent applications US 20010018414, US 2004220106, and US 200131005, U.S. Pat. No. 6,762,286 and U.S. Pat. No. 6,693,075 (University of Minnesota); and FVII variants as disclosed in WO 01/58935, U.S. Pat. No. 6,806,063, US patent application 20030096338 (Maxygen ApS), WO 03/93465 (Maxygen ApS), WO 04/029091 (Maxygen ApS), WO 04/083361 (Maxygen ApS), and WO 04/111242 (Maxygen ApS), as well as in WO 04/108763 (Canadian Blood Services).

Non-limiting examples of FVII variants having increased biological activity compared to wild-type FVIIa include FVII variants as disclosed in WO 01/83725, WO 02/22776, WO 02/077218, WO 03/027147, WO 04/029090, WO 05/075635, and European patent application with application number 05108713.8 (Novo Nordisk A/S), WO 02/38162 (Scripps Research Institute); and FVIIa variants with enhanced activity as disclosed in JP 2001061479 (Chemo-Sero-Therapeutic Res Inst.).

Examples of variants of factor VII include, without limitation, P10Q-FVII, K32E-FVII, P10Q/K32E-FVII, L305V-FVII, L305V/M306D/D309S-FVII, L3051-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157AF-VII, E296V-FVII, E296V/M298Q-FVII, V158D/E296V-FVII, V158D/M298K-FVII, and 5336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158D/E296V/M298Q/K337A-FVII, L305V/V158T/E296V/M298Q/K337A-FVII, S314E/K316H-FVII, S314E/K316Q-FVII, S314E/L305V-FVII, S314E/K337A-FVII, S314E/V158D-FVII, S314E/E296V-FVII, S314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q/K337A-FVII, S314E/L305V/V158T/E296V/

M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/M298Q-FVII, K316Q/L305V/V158T-FVII, K316Q/L305V/K337A/V158T-FVII, K316Q/L305V/K337A/M298Q-FVII, K316Q/L305V/K337A/E296V-FVII, K316Q/L305V/K337A/V158D-FVII, K316Q/L305V/V158D/M298Q-FVII, K316Q/L305V/V158D/E296V-FVII, K316Q/L305V/V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/E296V/M298Q-FVII, K316Q/L305V/V158T/K337A/M298Q-FVII, K316Q/L305V/V158T/E296V/K337A-FVII, K316Q/L305V/V158D/K337A/M298Q-FVII, K316Q/L305V/V158D/E296V/K337A-FVII, K316Q/L305V/V158D/E296V/M298Q/K337A-FVII, K316Q/L305V/V158T/E296V/M298Q/K337A-FVII, F374Y/K337A-FVII, F374Y/V158D-FVII, F374Y/E296V-FVII, F374Y/M298Q-FVII, F374Y/V158T-FVII, F374Y/S314E-FVII, F374Y/L305V-FVII, F374Y/L305V/K337A-FVII, F374Y/L305V/V158D-FVII, F374Y/L305V/E296V-FVII, F374Y/L305V/M298Q-FVII, F374Y/L305V/V158T-FVII, F374Y/L305V/S314E-FVII, F374Y/K337A/S314E-FVII, F374Y/K337A/V158T-FVII, F374Y/K337A/M298Q-FVII, F374Y/K337A/E296V-FVII, F374Y/K337A/V158D-FVII, F374Y/V158D/S314E-FVII, F374Y/V158D/M298Q-FVII, F374Y/V158D/E296V-FVII, F374Y/V158T/S314E-FVII, F374Y/V158T/M298Q-FVII, F374Y/V158T/E296V-FVII, F374Y/E296V/S314E-FVII, F374Y/S314E/M298Q-FVII, F374Y/E296V/M298Q-FVII, F374Y/L305V/K337A/V158D-FVII, F374Y/L305V/K337A/E296V-FVII, F374Y/L305V/K337A/M298Q-FVII, F374Y/L305V/K337A/V158T-FVII, F374Y/L305V/K337A/S314E-FVII, F374Y/L305V/V158D/E296V-FVII, F374Y/L305V/V158D/M298Q-FVII, F374Y/L305V/V158D/S314E-FVII, F374Y/L305V/E296V/M298Q-FVII, F374Y/L305V/E296V/V158T-FVII, F374Y/L305V/E296V/S314E-FVII, F374Y/L305V/M298Q/V158T-FVII, F374Y/L305V/M298Q/S314E-FVII, F374Y/L305V/V158T/S314E-FVII, F374Y/K337A/S314E/V158T-FVII, F374Y/K337A/S314E/M298Q-FVII, F374Y/K337A/S314E/E296V-FVII, F374Y/K337A/S314E/V158D-FVII, F374Y/K337A/V158T/M298Q-FVII, F374Y/K337A/V158T/E296V-FVII, F374Y/K337A/M298Q/E296V-FVII, F374Y/K337A/M298Q/V158D-FVII, F374Y/K337A/E296V/V158D-FVII, F374Y/V158D/S314E/M298Q-FVII, F374Y/V158D/S314E/E296V-FVII, F374Y/V158D/M298Q/E296V-FVII, F374Y/V158T/S314E/E296V-FVII, F374Y/V158T/S314E/M298Q-FVII, F374Y/V158T/M298Q/E296V-FVII, F374Y/E296V/S314E/M298Q-FVII, F374Y/L305V/M298Q/K337A/S314E-FVII, F374Y/L305V/E296V/K337A/S314E-FVII, F374Y/E296V/M298Q/K337A/S314E-FVII, F374Y/L305V/E296V/M298Q/K337A-FVII, M298Q/K337A-FVII, F374Y/L305V/E296V/M298Q/S314E-FVII, F374Y/V158D/E296V/M298Q/K337A-FVII, F374Y/V158D/E296V/M298Q/S314E-FVII, F374Y/L305V/V158D/K337A/S314E-FVII, F374Y/V158D/M298Q/K337A/S314E-FVII, F374Y/V158D/E296V/K337A/S314E-FVII, F374Y/L305V/V158D/E296V/M298Q-FVII, F374Y/L305V/V158D/E296V/K337A-FVII, F374Y/L305V/V158D/M298Q/S314E-FVII, F374Y/L305V/V158D/E296V/S314E-FVII, F374Y/V158T/E296V/M298Q/K337A-FVII, F374Y/V158T/E296V/M298Q/S314E-FVII, F374Y/L305V/V158T/K337A/S314E-FVII, F374Y/V158T/M298Q/K337A/S314E-FVII, F374Y/V158T/E296V/K337A/S314E-FVII, F374Y/L305V/V158T/E296V/M298Q-FVII, F374Y/L305V/V158T/M298Q/K337A-FVII, F374Y/L305V/V158T/E296V/K337A-FVII, F374Y/L305V/V158T/M298Q/S314E-FVII, F374Y/L305V/V158T/E296V/S314E-FVII, F374Y/E296V/M298Q/K337A/V158T/S314E-FVII, F374Y/V158D/E296V/M298Q/K337A/S314E-FVII, F374Y/L305V/V158D/E296V/M298Q/S314E-FVII, F374Y/L305V/E296V/M298Q/V158T/S314E-FVII, F374Y/L305V/E296V/M298Q/K337A/V158T-FVII, F374Y/L305V/E296V/K337A/V158T/S314E-FVII, F374Y/L305V/M298Q/K337A/V158T/S314E-FVII, F374Y/L305V/V158D/E296V/M298Q/K337A-FVII, F374Y/L305V/V158D/E296V/K337A/S314E-FVII, F374Y/L305V/V158D/M298Q/K337A/S314E-FVII, F374Y/E296V/M298Q/K337A/V158T/S314E-FVII, F374Y/L305V/V158D/E296V/M298Q/K337A/S314E-FVII,

S52A-Factor VII, S60A-Factor VII; R152E-Factor VII, S344A-Factor VII, T106N-FVII, K143N/N145T-FVII, V253N-FVII, R290N/A292T-FVII, G291N-FVII, R315N/V317T-FVII, K143N/N145T/R315N/V317T-FVII; and FVII having substitutions, additions or deletions in the amino acid sequence from 233Thr to 240Asn; FVII having substitutions, additions or deletions in the amino acid sequence from 304Arg to 329Cys; and FVII having substitutions, additions or deletions in the amino acid sequence from 153Ile to 223Arg.

Thus, substitution variants in a factor VII polypeptide include, without limitation substitutions in positions P10, K32, L305, M306, D309, L305, L305, F374, V158, M298, V158, E296, K337, M298, M298, S336, S314, K316, K316, F374, S52, S60, R152, S344, T106, K143, N145, V253, R290, A292, G291, R315, V317, and substitutions, additions or deletions in the amino acid sequence from T233 to N240 or from R304 to C329; or from I153 to R223, or combinations thereof, in particular variants such as P10Q, K32E, L305V, M306D, D309S, L305I, L305T, F374P, V158T, M298Q, V158D, E296V, K337A, M298Q, M298K, S336G, S314E, K316H, K316Q, F374Y, S52A, S60A, R152E, S344A, T106N, K143N, N145T, V253N, R290N, A292T, G291N, R315N, V317T, and substitutions, additions or deletions in the amino acid sequence from T233 to N240, or from R304 to C329, or from I153 to R223, or combinations thereof.

The biological activity of Factor VII (as Factor VIIa) in blood clotting derives from its ability to (i) bind to tissue factor (TF) and (ii) catalyze the proteolytic cleavage of Factor IX or Factor X to produce activated Factor IX or X (Factor IXa or Xa, respectively). Human Factor VIIa biological activity may be quantified by an assay measuring the ability of a preparation to promote blood clotting using Factor VII-deficient plasma and thromboplastin, as described, e.g., in U.S. Pat. No. 5,997,864. In this assay, biological activity is expressed as the reduction in clotting time relative to a control sample and is converted to "Factor VII units" by comparison with a pooled human serum standard containing 1 unit/ml Factor VII activity. Alternatively, Factor VII polypeptides may also be assayed for specific activities ("clot activity") by using a one-stage coagulation assay. For this purpose, the sample to be tested is diluted in 50 mM PIPES-buffer (pH 7.5), 0.1% BSA and 40 µl is incubated with 40 µl of Factor VII deficient plasma and 80 µl of human recombinant tissue factor containing 10 mM $Ca^{2+}$ and synthetic phospholipids. Coagulation times (clotting times) are measured and compared to a standard curve using a reference standard in a parallel line assay. Alternatively, Factor VIIa biological activity may be quantified by (i) measuring the ability of Factor VIIa to produce Factor Xa in a system comprising TF embedded in a lipid membrane and Factor X. (Persson et al., J. Biol. Chem. 272:19919-19924, 1997); (ii) measuring Factor X hydrolysis in an aqueous system; (iii) measuring its physical binding to TF using an instrument based on surface plasmon resonance (Persson, FEBS Letts. 413:359-363, 1997) and (iv) measuring hydrolysis of a synthetic substrate.

Factor VII variants having, in the activated (FVIIa) form, substantially the same or improved biological activity relative to wild-type Factor VIIa encompass those that exhibit at least about 10%, preferably at least about 25%, more preferably at least about 50%, even more preferably at least about 75% and most preferably at least about 90% of the specific activity of Factor VIIa that has been produced in the same cell type, when tested in one or more of a clotting assay, proteolysis assay or TF binding assay as described above.

In some embodiments, the Factor VII polypeptide is human Factor VIIa (hFVIIa), preferably recombinantly made human Factor VIIa (rhVIIa). In other embodiments, the Factor VII polypeptide is a Factor VII sequence variant. In some embodiments, the Factor VII polypeptide has a glycosylation different from wild-type human Factor VII. In some embodiments the Factor VII polypeptide is a Factor VII derivative, in particular a PEGylated Factor VII polypeptide, including a glycopegylated Factor VII polypeptide. In particular embodiments, the Factor VII polypeptide is a glycopegylated Factor VII polypeptide. In some embodiments thereof, the Factor VII polypeptide has been functionalised with a PEG moiety having a molecular weight of 5.000-50.000 Da, such as about 10.000 Da ("10K-PEG") or about 40.000 Da ("40K-PEG"). In a particular embodiment, the Factor VII polypeptide is glycopegylated human FVIIa wherein the PEG moiety has a molecular weight of about 10.000 Da ("10K-PEG-rFVIIa") or a molecular weight of about 40.000 Da ("40K-PEG-rFVIIa").

In various embodiments, e.g. those where the Factor VII polypeptide is a Factor VII-related polypeptide or a Factor VII sequence variant, the ratio between the activity of the Factor VII polypeptide and the activity of native human Factor VIIa (wild-type FVIIa) is at least about 1.25, preferably at least about 2.0, or 4.0, most preferred at least about 8.0, when tested in the "In Vitro Proteolysis Assay" (Assay 2) as described in the present specification. In some embodiments, the Factor VII polypeptides are Factor VII-related polypeptides, in particular variants, wherein the ratio between the activity of said Factor VII polypeptide and the activity of native human Factor VIIa (wild-type FVIIa) is at least about 1.25 when tested in the "In Vitro Hydrolysis Assay" (see Assay 1 below); in other embodiments, the ratio is at least about 2.0; in further embodiments, the ratio is at least about 4.0.

Processes for Preparation of Compounds of the Invention

Peptides of the present invention may be synthesized in accordance with well known techniques for peptide synthesis, such as the solid-phase synthetic technique initially described by Merrifield, in J. Am. Chem. Soc., 15: 2149-2154 (1963). Other peptide synthesis techniques may be found, for example, in M. Bodanszky et al., (1976) Peptide Synthesis, John Wiley & Sons, 2d Ed.; Kent and Clark-Lewis in Synthetic Peptides in Biology and Medicine, p. 295-358, eds. Alitalo, K., et al. Science Publishers, (Amsterdam, 1985); as well as other reference works known to those skilled in the art.

Compounds of formula (I) according to the invention may generally be prepared by the below described procedure:

Peptide Synthesis

The peptides were synthesized on Fmoc protected Rink amide resin (Novabiochem) (peptide amides) or on Wang resin (peptide acids) using Fmoc strategy on an Applied Biosystems 433A peptide synthesizer in 0.25 mmol scale using the manufacturer-supplied FastMoc UV protocols which employ HBTU-mediated couplings in NMP and UV monitoring of the deprotection of the Fmoc protection group. The protected amino acid derivatives used were standard Fmoc-amino acids (Anaspec) supplied in pre-weighed cartridges suitable for the ABI433A synthesizer. For peptide carbamates, the carbamoyl group was introduced either on solid phase or in solution after cleavage of the peptide from the support by treatment of the peptide with the succinimidyl carbonate of an alcohol or phenol, prepared by treatment of the corresponding alcohol or phenol with disuccinimidyl carbonate and DIPEA in MeCN (Gosh et al., Tetrahedron Lett 1992, 33 (20), 2781-2784). For peptide ureas, the aminocarbonyl group was introduced on solid phase by treatment of the resin-bound peptide with an isocyanate. In the case of acylated peptides, the last acylation was performed with the corresponding carboxylic acid using the same protocol as for the acylation with Fmoc-protected amino acids. The peptide can be cleaved from the resin by means of conventional methods, such as, e.g., by stirring at room temperature with a mixture of trifluoroacetic acid, water and triisopropylsilane (95:2.5:2.5). All the products were purified by preparative HPLC using conventional protocols, and quantified either by UV-absorbtion or by 1N NMR with an internal standard.

Pharmaceutical Formulation and Administration of Factor VII Polypeptides

In general, an aqueous, liquid Factor VII polypeptide formulation or composition of the invention (aqueous pharmaceutical composition of the invention) will—irrespective of whether the aqueous formulation is present in aqueous liquid form from the start, or is produced by dissolution/reconstitution of a substantially solid formulation (e.g. a lyophilized preparation) by addition of water or another aqueous carrier or vehicle—in general, suitably be administered parenterally, i.e., intravenously, subcutaneously, or intramuscularly, or by continuous or pulsatile infusion.

For use in human subjects, Factor VII polypeptide compositions of the invention for parenteral administration will, in addition to a compound of formula I or a physiologically tolerable salt thereof in an appropriate concentration, normally comprise the Factor VII polypeptide in combination with, preferably dissolved in, a pharmaceutically acceptable aqueous carrier. A variety of aqueous carriers may be used, such as water, buffered water, 0.4% saline, 0.3% glycine and the like. Factor VII polypeptides in the context of the invention may also be formulated into liposome preparations for delivery or targeting to the sites of injury. Liposome preparations are generally described in, e.g., U.S. Pat. No. 4,837,028, U.S. Pat. No. 4,501,728 and U.S. Pat. No. 4,975,282. The compositions may be sterilised by conventional, well-known sterilisation techniques. The resulting aqueous solutions may be packaged for use as such, or they may be filtered under aseptic conditions and lyophilized, the lyophilized preparation being combined with sterile water or a sterile aqueous solution (carrier, vehicle) prior to administration. The compositions may further contain pharmaceutically acceptable auxiliary substances as required to approximate physiological conditions and/or to enhance the chemical and/or physical stability of the composition. These include:

pH-adjusting and/or buffering agents, e.g. citrate (sodium or potassium), acetate (ammonium, sodium or calcium), histidine (L-histidine), malate, phosphate (sodium or potassium), tartaric acid, succinic acid, MES (2-N-morpholino-ethanesulfonic acid), HEPES (4-(2-hydroxy-ethyl)-piperazine-1-ethane-sulfonic acid), imidazole, TRIS [tris (hydroxymethyl)aminomethane], lactate, and glutamate. The buffer concentration range is chosen to maintain the preferred pH of the solution. The buffering agent may also be a mixture of two or more buffering agents, e.g. a mixture of two such agents, such that the mixture is able to provide a pH value in the specified range. In one embodiment, the buffer is a mixture of citrate and at least one of the buffers acetate (ammonium, sodium or calcium), histidine (L-histidine), malate, phosphate (sodium or potassium), tartaric acid, succinic acid, MES, HEPES, imidazole, TRIS, lactate and glutamate. The total concentration of buffer agent(s) is typically in the range of from about 1 mM to about 100 mM, such as from about 1 mM to about 50 mM, often from about 1 mM to about 25 mM, e.g. from about 2 mM to about 20 mM.

Calcium salts: the compositions—whether initially in liquid, freeze-dried or reconstituted form—may optionally contain a calcium salt. The calcium salt may be present in a low concentration, such as, e.g., from about 0.1 mM to about 5 mM; it may be present in a medium concentration, such as, e.g., from about 5 mM to about 15 mM; or it may be present in a higher concentration, such as, e.g., from about 15 mM to about 1000 mM. In one aspect, the calcium salt is selected from: calcium chloride, calcium acetate, calcium gluconate and calcium laevulate, and mixtures of two or more thereof. Alternatively, the concentration of calcium ions in the composition may be below 0.1 mM.

Tonicity-adjusting agents (tonicity-modifying substances which contribute to the osmolality of the formulation), e.g. amino acids, small peptides (having, e.g., from 2 to 5 amino acid residues), neutral salts, mono- or disaccharides, polysaccharides, sugar alcohols, or mixtures of at least two of such substances. Specific examples include, but are not limited to, sodium chloride, potassium chloride, sodium citrate, sucrose, glucose and mannitol. The concentration of tonicity-adjusting agent is adjusted to near isotonicity, depending on the other ingredients present in the formulation. In general, tonicity-adjusting agents are incorporated in a concentration of from about 1 to about 500 mM, such as from about 1 to about 300 mM, often from about 10 to about 200 mM, e.g. from about 20 to about 150 mM, depending on the other ingredients present. Neutral salts such as, e.g., sodium chloride or potassium chloride may be used. The term "neutral salt" indicates a salt that is substantially neither acidic nor basic, i.e. has little or no effect on formulation pH when dissolved.

Surfactants, typically a non-ionic surfactant, suitably of the polysorbate or Tween™ type (e.g. Polysorbate™ 20 or 80, or Tween™ 80), or of the poloxamer or Pluronic™ type (e.g. Poloxamer™ 188 or 407). The amount of surfactant incorporated may typically range from about 0.005 to about 1% weight/weight (w/w), with amounts of from about 0.005 to about 0.1% w/w, such as from about 0.005 to 0.02% w/w, typically being preferred. In some situations, relatively high concentrations, e.g. up to about 0.5% w/w, are desirable to maintain protein stability. However, the levels of surfactant used in actual practice are customarily limited by clinical practice.

Antioxidants, e.g. ascorbic acid, cysteine, homocysteine, cystine, cysstathionine, methionine, glutathione, or peptides containing cysteine or methionine; methionine, in particular L-methionine, is typically a very suitable antioxidant. An antioxidant is typically incorporated in a concentration of from about 0.1 to about 2 mg/ml.

Preservatives (included in the formulation to retard microbial growth, thereby permitting, for example, "multiple use" packaging of the FVII polypeptide). Examples of preservatives include phenol, benzyl alcohol, ortho-cresol, meta-cresol, para-cresol, methylparaben, propylparaben, benzalconium chloride, and benzethonium chloride. A preservative is typically incorporated in a concentration of from about 0.1 to about 2 mg/ml, depending on the pH range and type of preservative.

The concentration of Factor VII polypeptide in the compositions can vary widely, typically from about 0.01% w/w to about 2% w/w (i.e. from about 0.1 mg/ml to about 20 mg/ml), such as from about 0.05% w/w to about 1.5% w/w (i.e. from about 0.5 mg/l to about 15 mg/ml), e.g. from about 0.05% w/w to about 1% w/w (i.e. from about 0.5 mg/ml to about 10 mg/ml), and will be selected primarily on the basis of fluid volumes, viscosities, etc., in accordance with the particular mode of administration selected. In the case of Factor VIIa, concentration is frequently expressed as mg/ml or as International units/ml (IU/ml). 1 mg of FVIIa usually corresponds to 43000-56000 IU or more.

The concentration of a compound (or compounds) of formula I of the invention in a liquid, aqueous pharmaceutical composition of the invention will typically be at least 1 µM. The desirable (or necessary) concentration typically depends on the selected compound (or compounds), more specifically on the binding affinity of the selected compound(s) to the Factor VII polypeptide. In various embodiments, the compound of formula I may be present in a concentration of at least 5 µM, at least 10 µM, at least 20 µM, at least 50 µM, at least 100 µM, at least 150 µM, at least 250 µM, at least 500 µM, at least 1 mM, at least 2 mM, at least 4 mM, at least 5 mM, at least 8 mM, at least 9 mM, at least 10 mM, at least 15 mM, or at least 20 mM, such as, e.g., in the range of 1-10000 µM, 10-10000 µM, 20-10000 µM, 50-10000 µM, 10-5000 µM, 10-2000 µM, 20-5000 µM, 20-2000 µM, 50-5000 µM, 0.1-100 mM, 0.1-75 mM, 0.1-50 mM, 0.1-10 mM, 0.2-75 mM, 0.2-50 mM, 0.2-20 mM, 0.5-75 mM or 0.5-50 mM.

In various embodiments, the molar ratio between the compound of formula I and FVII polypeptide may be: above 0.1, above 0.5, above 1, above 2, above 5, above 10, above 25, above 100, above 250, above 1000, above 2500, or above 5000, such as, e.g., in the range of 0.1-10000, 0.1-5000, 0.1-2500, 0.1-1000, 0.1-250, 0.1-100, 0.1-25, 0.1-10, 0.5-10000, 0.5-5000, 0.5-2500, 0.5-1000, 0.5-250, 0.5-100, 0.5-25, 0.5-10, 1-10000, 1-5000, 1-2500, 1-1000, 1-250, 1-100; 1-25; 1-10, 10-10000, 10-5000, 10-250, 1000-10000, or 1000-5000.

Methods for preparing parenterally administrable compositions will be known or apparent to those skilled in the art, and are described in more detail in, for example, Remington's Pharmaceutical Sciences, 18th edition, Mack Publishing Company, Easton, Pa. (1990).

For treatment in connection with deliberate interventions (e.g. surgical procedures), Factor VII polypeptides will typically be administered within about 24 hours prior to performing the intervention, and for as much as 7 days or more thereafter.

Administration as a coagulant can be by a variety of routes as described herein. The dose of Factor VII polypeptide (e.g. rhFVIIa) will normally range from about 0.05 mg/day to 500 mg/day, preferably from about 1 mg/day to about 200 mg/day, and more preferably from about 10 mg/day to about 175 mg/day for a 70 kg subject as loading and maintenance doses, depending on the weight of the subject and the severity of the condition.

Compositions containing Factor VII polypeptides may be administered for prophylactic and/or therapeutic treatments. In therapeutic applications, compositions are administered to a subject already suffering from a condition, as described above, in an amount sufficient to cure, alleviate or partially arrest the condition and its complications. An amount adequate to accomplish this is defined as a "therapeutically effective amount". As will be understood by the person skilled in the art, amounts effective for this purpose will depend on the severity of the condition or injury, as well as on the body weight and general physical condition of the subject.

It should be borne in mind that pharmaceutical compositions of FVII polypeptides (e.g. rhFVIIa) are generally employed in connection with life-threatening or potentially life-threatening medical conditions or states, and in such circumstances—in view of the general advantages associated with minimizing quantities of extraneous substances, and taking into account the general lack of immunogenicity of human Factor VII polypeptides—it is possible and may be felt desirable by the treating physician to administer a substantial excess of the Factor VII polypeptide in question.

In prophylactic applications, compositions containing a Factor VII polypeptide are administered to a subject susceptible to or otherwise at risk of a disease state or injury in order to enhance the subject's own coagulative capability. The dosage employed for such purposes (which may be termed a "prophylactically effective dose") will once again depend on the subject's body weight and general state of health, but will once again generally range from about 0.05 mg/day to about 500 mg/day, more commonly from about 1.0 mg/day to about 200 mg/day for a 70-kilogram subject.

In the case, specifically, of administration of rhFVIIa to human subjects, dosage levels have generally been in the range of about 90-120 µg/kg body weight per dose. However, there is a current preference for somewhat higher doses, e.g. doses in excess of 150 µg/kg body weight, and in some cases doses of about 250-300 µg/kg.

Single or multiple administration of the composition in question may be carried out using dose levels and dosing regimens selected by the treating physician. For outpatients requiring daily maintenance levels, a Factor VII polypeptide may be administered by continuous infusion, e.g. using a portable pump system.

Local administration of a Factor VII polypeptide, e.g. topical application, may be carried out, e.g., by spraying, by perfusion, by use of a double balloon catheter or a stent, by incorporation into vascular grafts or stents, in the form of hydrogels to coat balloon catheters, or by other well established methods. In any event, the pharmaceutical composition in question should provide a quantity of Factor VII polypeptide which is adequate to effectively treat the subject.

The liquid pharmaceutical preparation should typically be stable for at least six months, and preferably up to 36 months, when stored at temperatures ranging from 2° C. to 8° C. It should be understood that the liquid pharmaceutical preparation preferably is stable even at higher temperatures, such as ambient temperature, e.g. 20° C. to 30° C., although this often requires a higher content of the inhibitor.

The term "stable" is intended to denote that after storage for 6 months at 2° C. to 8° C. the initial liquid pharmaceutical preparation retains at least 50% of its initial biological activity. Preferably, the liquid pharmaceutical preparation retains at least 70%, such as at least 80%, or at least 85%, or at least 90%, or at least 95%, of its initial activity after storage for 6 months at 2 to 8° C.

With respect to Factor VII polypeptides, the term "stable" is more particularly intended to denote that (i) after storage for 6 months at 2° C. to 8° C. the initial liquid pharmaceutical preparation retains at least 50% of its initial biological activity as measured by a one-stage clot assay (Assay 4), or (ii) after storage for 6 months at 2° C. to 8° C., the content of heavy chain degradation products is at the most 40% (w/w) assuming that the initial liquid pharmaceutical preparation comprises no heavy chain degradation products (i.e. only the Factor VII polypeptide is entered into the calculation of the percentage). Preferably, the initial liquid pharmaceutical preparation retains at least 70%, such as at least 80%, or at least 85%, or at least 90%, or at least 95%, of its initial activity after storage for 6 months at 2-8° C. Also preferably, the content of heavy chain degradation products in the initial liquid pharmaceutical preparation is at the most 30% (w/w), at the most 25% (w/w), at the most 20% (w/w), at the most 15% (w/w), at the most 10% (w/w), at the most 5% (w/w), or at the most 3% (w/w).

Hence, as outlined above, a "stabilized composition" refers to a composition with increased physical stability, increased chemical stability or increased physical and chemical stability. In general, a composition must be stable during use and storage (in compliance with recommended use and storage conditions) until the expiration date is reached.

In one embodiment the pharmaceutical composition comprising the FVII polypeptide and a compound of formula (I) is stable for more than 6 months of storage (at 2-8° C.) and for more than 1 week of usage at ambient temperature. In a further embodiment the pharmaceutical composition comprising the FVII polypeptide and a compound of formula (I) is stable for more than 24 months of storage (at 2-8° C.) and for more than 4 weeks of usage at ambient temperature. In another, further embodiment the pharmaceutical composition comprising the FVII polypeptide and a compound of formula (I) is stable for more than 36 months of storage (at 2-8° C.) and for more than 6 weeks of usage at ambient temperature.

As will be understood, the liquid, aqueous pharmaceutical compositions defined herein can be used in the field of medicine. Thus, the present invention in particular provides the liquid, aqueous pharmaceutical compositions defined herein for use as a medicament, more particular for use as a medicament for treating condition or disorder against which said Factor VII polypeptide is effective.

Consequently, the present invention also provides the use of the liquid, aqueous pharmaceutical composition as defined herein for the preparation of a medicament for treating a condition or disorder against which said Factor VII polypeptide is effective, as well as a method for treating a condition or disorder against which said Factor VII polypeptide is effective, the method comprising administering to a subject in need thereof an effective amount of the liquid, aqueous pharmaceutical composition as defined herein.

The preparations of the present invention may be used to treat any condition or disorder against which said Factor VII polypeptide is effective, such as, without limitation, bleeding disorders, including those caused by clotting factor deficiencies (e.g., congenital haemophilia A with and without inhibitors, acquired haemophilia A, congenital haemophilia B with and without inhibitors, acquired haemophilia B, coagulation Factor XI deficiency, coagulation Factor VII deficiency), von Willebrand's disease, platelet disorders or deficiencies (e.g., low platelet count), or thrombocytopenia. As used herein the term "bleeding disorder" reflects any defect, congenital, acquired or induced, of cellular or molecular origin that is manifested in bleedings. Conditions or disorders against which said Factor VII polypeptide is effective also include bleedings in subjects who experience extensive tissue damage, e.g. in association with surgery or trauma including, without limitation, bleedings associated with spinal or cardiac surgery, orthopedic surgery (e.g. hips, elbows, knees), or laparoscopic surgery, penetrating or blunt trauma, head trauma including traumatic brain injury, intracerebral haemorrhage, bleedings associated with induced defective haemostasis, such as bleedings associated with anticoagulant therapy or antifibrinolytic therapy, and uncontrolled and excessive bleeding from any cause. In case of extensive tissue damage, the normal haemostatic mechanism may be overwhelmed by the demand of immediate haemostasis and bleedings may develop in spite of an otherwise normal haemostatic mechanism. Included are also bleedings in organs with limited possibility for surgical haemostasis such as e.g. the brain, inner ear region, eyes, liver, lung, tumour tissue, and gastrointestinal tract as well as when bleeding is diffuse (haemorrhagic gastritis and profuse uterine bleeding). Common for all these situations is the difficulty to provide haemostasis by surgical techniques (sutures, clips, etc.).

The term "effective amount" is the effective dose to be determined by a qualified practitioner, who may titrate dosages to achieve the desired response. Factors for consideration of dose will include potency, bioavailability, desired pharmacokinetic/pharmacodynamic profiles, condition of treatment, patient-related factors (e.g. weight, health, age, etc.), presence of co-administered medications (e.g., anticoagulants), time of administration, or other factors known to a medical practitioner.

The term "treatment" is defined as the management and care of a subject, e.g. a mammal, in particular a human, for the purpose of combating the disease, condition, or disorder and includes the administration of a Factor VII polypeptide to prevent the onset of the symptoms or complications, or alleviating the symptoms or complications, or eliminating the disease, condition, or disorder. Pharmaceutical compositions according to the present invention containing a Factor VII polypeptide may be administered parenterally to subjects in need of such a treatment. Parenteral administration may be performed by subcutaneous, intramuscular or intravenous injection by means of a syringe, optionally a pen-like syringe. Alternatively, parenteral administration can be performed by means of an infusion pump.

In important embodiments, the pharmaceutical composition is adapted to subcutaneous, intramuscular or intravenous injection according to methods known in the art.

The pharmaceutical composition comprising a Factor VII polypeptide and one or more compounds (I) according to the present invention may further contain, or be used in conjunction with, one or more coagulation factors, such as, without limitation, Factor XIII, Factor VIII, Factor IX, another Factor VII polypeptide, or FEIBA™.

FURTHER ASPECTS OF THE INVENTION

As already indicated to some extent above, further aspects of the present invention include the following:

A pharmaceutical composition (e.g. a liquid, aqueous pharmaceutical composition) comprising: one or more compounds, or physiologically tolerable salts thereof, according to the invention; and a Factor VII polypeptide (e.g. wild-type human FVIIa, such as rhFVIIa).

A method of preparing a composition comprising a Factor VII polypeptide (e.g. wild-type human FVIIa, such as rhFVIIa), comprising: adding a compound, or a physiologically tolerable salt thereof, according to the invention to a sample containing the Factor VII polypeptide; or adding the Factor VII polypeptide to a sample containing a compound, or a physiologically tolerable salt thereof, according to the invention; in a method of this type, the compound or salt thereof and/or the Factor VII polypeptide may be present in a liquid, aqueous medium.

A pharmaceutical composition prepared by a method according to the invention;

A method of inhibiting a Factor VII polypeptide (e.g. wild-type FVIIa, such as rhFVIIa), comprising: adding a compound, or a physiologically tolerable salt thereof, according to the invention to a sample containing the Factor VII polypeptide; or adding the Factor VII polypeptide to a sample containing a compound, or a physiologically tolerable salt thereof, according to the invention; in a method of this type, the compound or salt thereof and/or the Factor VII polypeptide may be present in a liquid, aqueous medium.

A use of a pharmaceutical composition according to the invention for the manufacture of a medicament for the treatment of a condition or disorder against which the Factor VII polypeptide in question is effective.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (for instance all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language ("for instance", "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (for instance a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

EXAMPLES

The following abbreviations are used:
Abu: α-aminobutyric acid
Ac: acetyl
Aib α-aminoisobutyric acid
Alle allo-isoleucine
Alloc allyloxycarbonyl
4-amidino-Phe 4-amidino-phenylalanine, $H_2N$—$CH(CH_2$—$C_6H_4$—$C(=NH)NH_2)$—$CO_2H$
Boc: tert-butyloxycarbonyl
t-Bu tert-butyl
Cha β-cyclohexylalanine, (1S)-1-amino-2-cyclohexylpropionic acid
DCM: dichloromethane, methylenechloride
DIPEA or DIEA diisopropylethylamine
DMF: N,N-dimethyl formamide
DMSO: dimethyl sulfoxide
EDAC: N-ethyl-N'-(3-dimethylaminopropyl)carbodiimide hydrochloride
ELS: evaporative light scattering
Et: ethyl
Fmoc 9H-fluoren-9-ylmethoxycarbonyl
HBTU 2-(1H-Benzotriazol-1-yl-)-1,1,3,3 tetramethyluronium hexafluorophosphate
HOBt: N-hydroxybenzotriazole, 1-hydroxybenzotriazole
HomoArg: homo-arginine, N-epsilon-amidinolysine, $H2N$—$CH((CH2)4$-$NH$—$C(=NH)NH_2)CO_2H$
Hph: homophenylalanine
Me: methyl
Nle norleucine, α-aminocaproic acid
NMP: N-methylpyrrolidone
Nva norvaline, α-aminovaleric acid
HPLC: high pressure liquid chromatography
LCMS: liquid chromatography coupled with mass spectrometry
Lys(mPeg(1-10k)-CO): lysine acylated at the side-chain amino group with a methoxypoly(ethylene glycol)-derived carboxylic acid (MeO—$(CH_2$—$CH_2$—$O)_n$—$(CH_2)_m$—$CO_2H$)
NMP: N-methyl-2-pyrrolidinone
Phg (S)-phenylglycine, L-phenylglycine
Pmc: 2,2,5,7,8-pentamethylchroman-6-sulfonyl
r.t. room temperature
Su: succinimidyl
TFA: trifluoroacetic acid
TIS: triisopropylsilane
Trt: trityl General Methods
Procedures
(1) Enzyme Inhibition—General The ability of compounds of formula (I) to inhibit FVIIa or other enzymes/factors, such as, e.g., Factor Xa, thrombin, plasmin, or trypsin, is assessed by determining the concentration of the compound of formula (I) that inhibits the activity of the enzyme in question by 50%, i.e. the $IC_{50}$ value, which is related to the inhibition constant Ki. This $IC_{50}$ value is determined with the aid of a suitable chromogenic substrate, and calculated by linear regression after plotting the relative rates of hydrolysis (compared to the uninhibited control) versus the log of the concentration of compound of formula (I). For calculating the inhibition constant Ki, correction of the $IC_{50}$ value for competition with substrate is taken account of by using the formula:

$Ki=IC_{50}/\{1+(\text{substrate concentration}/Km)\}$, where Km is the Michaelis-Menten constant [Chen and Prusoff, Biochem. Pharmacol. 22 (1973), 3099-3108; I. H. Segal, Enzyme Kinetics, 1975, John Wiley & Sons, New York, 100-125; both of which references are incorporated herein in their entirety by reference].

(1)a Factor VIIa (FVIIa) Assay

The inhibitory activity [expressed as inhibition constant Ki(FVIIa)] of compounds of formula I towards Factor VIIa/tissue factor activity may be determined using a chromogenic assay essentially as described previously [J. A. Ostrem et al., Biochemistry 37 (1998) 1053-1059, which reference is incorporated herein in its entirety by reference). Kinetic assays are conducted at 25° C. in half-area microtiter plates (Costar Corp., Cambridge, Mass.) using a kinetic plate reader (Molecular Devices Spectramax 250). In a typical assay, 25 µl rhFVIIa and TF (final concentrations 5 nM and 10 nM, respectively) are combined with 40 µl of inhibitor dilutions in 10% DMSO/TBS-PEG buffer (50 mM Tris, 15 mM NaCl, 5 mM $CaCl_2$, 0.05% PEG 8000, pH 8.15). Following a 15 minute preincubation period, the assay is initiated by the addition of 35 µl of the chromogenic substrate S-2288 (D-Ile-Pro-Arg-p-nitroanilide, Pharmacia Hepar Inc., 500 µM final concentration). The compounds of the present invention inhibit FVIIa/TF with $IC_{50}$-values ranging from 3 mM to <1 µM.

The following assays (1)b-e and (2)a-c may be employed to investigate the possible inhibition of certain other coagulation enzymes and other serine proteases by compounds of formula I, and thus to determine the specificity of compounds of formula I.

(I)b Factor Xa Assay

A TBS-PEG buffer of composition 50 mM Tris-Cl, pH 7.8, 200 mM NaCl, 0.05% (w/v) PEG-8000, 0.02% (w/v) NaN3) is used for this assay. The $IC_{50}$ is determined by combining: 25 µl human factor Xa (Enzyme Research Laboratories, Inc.; South Bend, Ind.) in TBS-PEG buffer; 40 µl 10% (v/v) DMSO in TBS-PEG buffer (uninhibited control) or various concentrations of the compound to be tested diluted in 10% (v/v) DMSO in TBS-PEG; and substrate S-2765 [N(α)-benzyloxycarbonyl-D-Arg-Gly-L-Arg-p-nitroanilide; Kabi Pharmacia, Inc.; Franklin, Ohio] in TBS-PEG, in appropriate wells of a Costar half-area microtiter plate.

The assay is performed by pre-incubating the compound of formula I plus enzyme for 10 min. The assay is then initiated by adding substrate to obtain a final volume of 100 µl. The initial velocity of chromogenic substrate hydrolysis is measured by the change in absorbance at 405 nm using a Bio-tek Instruments kinetic plate reader (Ceres UV900HDi) at 25° C. during the linear portion of the time course (usually 1.5 min after addition of substrate). The enzyme concentration is 0.5 nM, and substrate concentration is 140 µM.

(1)c Thrombin Assay

TBS-PEG buffer is likewise used in this assay. The $IC_{50}$ is determined as above for the Factor Xa assay, except that the substrate employed is S-2366 (L-PyroGlu-L-Pro-L-Arg-p-nitroanilide; Kabi) and the enzyme is human thrombin (Enzyme Research Laboratories, Inc.; South Bend, Ind.). The enzyme concentration is 175 µM.

(1)d Plasmin Assay

TBS-PEG buffer is likewise used in this assay. The $IC_{50}$ is determined as described above for the Factor Xa assay, except that the substrate employed is S-2251 (D-Val-L-Leu-L-Lys-p-nitroanilide; Kabi) and the enzyme is human plasmin (Kabi). The enzyme concentration is 5 nM and the substrate concentration is 300 µM.

(1)e Trypsin Assay

TBS-PEG buffer containing 10 mM $CaCl_2$ is used for this assay. The $IC_{50}$ is determined as described above for the Factor Xa assay, except that the substrate employed is BAPNA (benzoyl-L-Arg-p-nitroanilide; Sigma Chemical Co.; St. Louis, Mo.) and the enzyme is bovine pancreatic trypsin (Type XIII, TPCK treated; Sigma). The enzyme concentration is 50 nM and the substrate concentration is 300 µM.

(2)a Amidolytic Assays for FIXa and tPA.

Enzymes and substrates are from American Diagnostica; FIXa (cat no 449b), FIXa substrate (cat no 299F), tPA (cat no 170) and tPA substrate (cat no 444LF). Hydrolysis of substrates 299F and 444LF is followed in a Spectramax Fluorimeter at 360 nm excitation and 440 nm emission. Hydrolysis of substrate 251 and S-2288 was followed in a Spectramax Spectrophotometer at 405 nm.

All assays are performed in a buffer consisting of 50 mM Hepes pH 7.4, 100 mM NaCl, 5 mM $CaCl_2$, 0.01% Tween80. Inhibitors are used at 10, 20, 50, 100, 200 µM concentration. The FIXa assay is performed using 100 µM substrate, the tPA assay is performed using 10 µM substrate.

(2)b Amidolytic Assays for FXIa and FXIIa

The enzymes FXIa and FXIIa are from American Diagnostica; FXIa (cat no 4011a), FXIIa (cat no 412HA) and trypsin (cat no 20465) are from Life Technology. The chromogenic substrates (Chromogenix) in use are 2288 for FXIa and 2765 for FXIIa. Hydrolysis of the chromogenic substrates is followed in a Spectramax Spectrophotometer at 405 nm for 10-20 min with intervals of 5-20 sec depending on the enzyme.

All assays are performed in a buffer consisting of 50 mM Hepes pH 7.4, 100 mM NaCl, 5 mM $CaCl_2$, 0.01% BSA. With the exception that for the FIXa assays ethylene glycol is further added to a final concentration of 40%. In the assays substrate concentrations of 50, 100, 200, 500, 1000 µM are employed for each inhibitor concentration: 25, 50, 100, 500 µM.

(2)c Data Analysis

For the assays run at a single substrate concentration, KI is determined using the formula V0/VI=1+I/KI (valid for S<<Km), by linear fitting of the values determined at several different inhibitor concentrations. V0 is the rate of hydrolysis without inhibitors present, VI is the rate of hydrolysis at the in the presence of inhibitor and I is the inhibitor concentration. From double reciprocal plots of 1/v versus 1/s for each inhibitor concentration the slope (Km(app)/V) is determined. This is followed by plots of Km(app)/V against the inhibitor concentration. Ki is determined as the intercept of the straight line at the i-axis.

Stabilizing Effect of a Compound of Formula (I) on FVIIa

To measure the stabilizing effect of a compound of formula (I) on FVIIa, the biological activity of a FVII polypeptide, such as FVIIa, may be measured using a one-stage coagulation assay. For this purpose, the sample to be tested is diluted in 50 mM PIPES-buffer (pH 7.5), 0.1% BSA, and 40 µl of this solution is incubated with 40 µl of FVII-deficient plasma and 80 µl of human recombinant TF containing 10 mM $Ca^{2+}$ and synthetic phospholipids. Coagulation times are measured and compared to a standard curve using a reference standard in a parallel line assay.

Assays Suitable for Determining Biological Activity of Factor VII Polypeptides

Factor VII polypeptides useful in accordance with the present invention may be selected by suitable assays that can be performed as simple preliminary in vitro tests. Thus, the present specification discloses a simple test (entitled "In Vitro Hydrolysis Assay") for the activity of Factor VII polypeptides.

1st Generation Clot Assay

The activity of the Factor VII polypeptides may be measured using a one-stage clot assay essentially as described in WO 92/15686 or U.S. Pat. No. 5,997,864. Briefly, the sample to be tested is diluted in 50 mM Tris (pH 7.5), 0.1% BSA and 100 µL is incubated with 100 µL of Factor VII deficient plasma and 200 µL of thromboplastin C containing 10 mM $Ca^{2+}$. Clotting times are measured and compared to a standard curve using a reference standard or a pool of citrated normal human plasma in serial dilution.

In Vitro Hydrolysis Assay (Assay 1)

Native (wild-type) Factor VIIa and Factor VII polypeptide (both hereinafter referred to as "Factor VIIa") may be assayed for specific activities. They may also be assayed in parallel to directly compare their specific activities. The assay is carried out in a microtiter plate (MaxiSorp, Nunc, Denmark). The chromogenic substrate D-Ile-Pro-Arg-p-nitroanilide (S-2288, Chromogenix, Sweden), final concentration 1 mM, is added to Factor VIIa (final concentration 100 nM) in 50 mM HEPES, pH 7.4, containing 0.1 M NaCl, 5 mM $CaCl_2$ and 1 mg/mL bovine serum albumin. The absorbance at 405 nm is measured continuously in a SPECTRAMAX™ 340 plate reader (Molecular Devices, USA). The absorbance developed during a 20-minute incubation, after subtraction of the absorbance in a blank well containing no enzyme, is used for calculating the ratio between the activities of Factor VII polypeptide and wild-type Factor VIIa:

Ratio=(A405 nm Factor VII polypeptide)/(A405 nm Factor VIIa wild-type). Based thereon, Factor VII polypeptides with an activity lower than, comparable to, or higher than native Factor VIIa may be identified, such as, for example, Factor VII polypeptides where the ratio between the activity of the Factor VII polypeptide and the activity of native Factor VII (wild-type FVII) is about 1.0 versus above 1.0.

The activity of the Factor VII polypeptides may also be measured using a physiological substrate such as Factor X ("In Vitro Proteolysis Assay"), suitably at a concentration of 100-1000 nM, where the Factor Xa generated is measured after the addition of a suitable chromogenic substrate (eg. S-2765). In addition, the activity assay may be run at physiological temperature.

In Vitro Proteolysis Assay (Assay 2)

Native (wild-type) Factor VIIa and Factor VII polypeptide (both hereinafter referred to as "Factor VIIa") are assayed in parallel to directly compare their specific activities. The assay is carried out in a microtiter plate (MaxiSorp, Nunc, Denmark). Factor VIIa (10 nM) and Factor X (0.8 microM) in 100 µL 50 mM HEPES, pH 7.4, containing 0.1 M NaCl, 5 mM CaCl$_2$ and 1 mg/mL bovine serum albumin, are incubated for 15 min. Factor X cleavage is then stopped by the addition of 50 µL 50 mM HEPES, pH 7.4, containing 0.1 M NaCl, 20 mM EDTA and 1 mg/mL bovine serum albumin. The amount of Factor Xa generated is measured by the addition of the chromogenic substrate Z-D-Arg-Gly-Arg-p-nitroanilide (S-2765, Chromogenix, Sweden), final concentration 0.5 mM. The absorbance at 405 nm is measured continuously in a SPECTRAMAX™ 340 plate reader (Molecular Devices, USA). The absorbance developed during 10 minutes, after subtraction of the absorbance in a blank well containing no FVIIa, is used for calculating the ratio between the proteolytic activities of Factor VII polypeptide and wild-type Factor VIIa:

Ratio=(A405 nm Factor VII polypeptide)/(A405 nm Factor VIIa wild-type). Based thereon, a Factor VII polypeptide with an activity lower than, comparable to, or higher than native Factor VIIa may be identified, such as, for example, Factor VII polypeptides where the ratio between the activity of the Factor VII polypeptide and the activity of native Factor VII (wild-type FVII) is about 1.0 versus above 1.0.

Thrombin Generation Assay (Assay 3)

The ability of a Factor VII polypeptides to generate thrombin can be measured in an assay (Assay 3) comprising all relevant coagulation Factors and inhibitors at physiological concentrations (minus Factor VIII when mimicking hemophilia A conditions) and activated platelets (as described on p. 543 in Monroe et al. (1997) Brit. J. Haematol. 99, 542-547 which is hereby incorporated as reference).

One-Stage Coagulation Assay (Clot Assay) (Assay 4)

Factor VII polypeptides may also be assayed for specific activities ("clot activity") by using a one-stage coagulation assay (Assay 4). For this purpose, the sample to be tested is diluted in 50 mM PIPES-buffer (pH 7.2), 1% BSA and 40 µl is incubated with 40 µl of Factor VII deficient plasma and 80 µl of human recombinant tissue factor containing 10 mM Ca$^{2+}$ and synthetic phospholipids. Coagulation times (clotting times) are measured and compared to a standard curve using a reference standard in a parallel line assay.

Content of Heavy Chain Degradation Product, Oxidized Forms, and Aggregates

Content of oxidized forms and heavy chain degradation products is determined by RP-HPLC as described in the following: Reverse phase HPLC was run on a proprietary 4.5×250 mm butyl-bonded silica column with a particle size of 5 µm and pore size 300 Å. Column temperature: 70° C. A-buffer: 0.1% v/v trifluoracetic acid. B-buffer: 0.09% v/v trifluoracetic acid, 80% v/v acetonitrile. The column was eluted with a linear gradient from X to (X+13) % B in 30 minutes. X was adjusted so that FVIIa elutes with a retention time of approximately 26 minutes. Flow rate: 1.0 mL/min. Detection: 214 nm. Load: 25 µg FVIIa.

The content of aggregates is determined by non-denaturing size exclusion HPLC: Non-denaturing size exclusion chromatography was run on a Waters Protein Pak 300 SW column, 7.5×300 mm using 0.2 M ammoniumsulfat, 5% 2-propanol pH 7.0 as mobile phase. Flow rate: 0.5 ml/min. Detection: 215 nm. Load: 25 µg FVIIa.

NMR Analysis

NMR spectra were recorded on Bruker 300 MHz and 400 MHz instruments. HPLC-MS was performed on a Perkin Elmer instrument (API 100).

HPLC Analysis

HPLC-systems from Merck-Hitachi (Hibar™ RT 250-4, Lichrosorb™ RP 18, 5.0 µm, 4.0×250 mm, gradient elution, 20% to 80% acetonitrile in water within 30 min, 1.0 ml/min, detection at 254 nm) and Waters (Symmetry™, C18, 3.5 µm, 3.0×150 mm, gradient elution, 5% to 90% acetonitrile in water within 15 min, 1.0 ml/min, detection at 214 nm) were used.

Peptide Synthesis

The peptides were synthesized on Fmoc protected Rink amide resin (Novabiochem) (peptide amides) or on Wang resin (peptide acids) using Fmoc strategy on an Applied Biosystems 433A peptide synthesizer in 0.25 mmol scale using the manufacturer-supplied FastMoc UV protocols which employ HBTU-mediated couplings in NMP and UV monitoring of the deprotection of the Fmoc protection group. The protected amino acid derivatives used were standard Fmoc-amino acids (Anaspec) supplied in preweighed cartridges suitable for the ABI433A synthesizer. Protected (Fmoc or Boc) 4-amidino-Phe was commercially available, or prepared using a procedure from the literature (Pearson et al., J. Med. Chem. 1996, 39, 1372-1382). For peptide carbamates, the carbamoyl group was introduced either on solid phase or in solution after cleavage of the peptide from the support by treatment of the peptide with the succinimidyl carbonate of an alcohol or phenol, prepared by treatment of the corresponding alcohol or phenol with disuccinimidyl carbonate and DIPEA in MeCN (Gosh et al., Tetrahedron Lett 1992, 33 (20), 2781-2784). For peptide ureas, the aminocarbonyl group was introduced on solid phase by treatment of the resin-bound peptide with an isocyanate. In the case of acylated peptides, the last acylation was performed with the corresponding carboxylic acid using the same protocol as for the acylation with Fmoc-protected amino acids.

Procedure for Cleaving the Peptide from the Resin:

The peptide was cleaved from the resin by stirring for 180 min at room temperature with a mixture of trifluoroacetic acid, water and triisopropylsilane (95:2.5:2.5). The cleavage mixture was filtered and the filtrate was concentrated to an oil by a stream of nitrogen. The crude peptide was precipitated from this oil with diethyl ether (45 ml) and washed three times with diethyl ether (45 ml each).

Purification:

The crude peptide was purified by semipreparative HPLC on a 20 mm×250 mm column packed with C-18 silica. Depending on the peptide one or two of the following purification systems were used.

TFA:

After drying, the crude peptide was dissolved in 5 ml 50% acetic acid/H$_2$O and diluted to 20 ml with H$_2$O, injected, and eluted with a gradient of 40-60% CH$_3$CN in 0.1% TFA 10 ml/min during 50 min at 40° C. The peptide-containing fractions were collected. The purified peptide was lyophilized after dilution of the eluate with water.

Ammonium Sulphate:

The column was equilibrated with 40% CH$_3$CN in 0.05M (NH$_4$)$_2$SO$_4$, which was adjusted to pH 2.5 with concentrated H$_2$SO$_4$. After drying, the crude peptide was dissolved in 5 ml 50% acetic acid/H$_2$O and diluted to 20 ml with H$_2$O, injected, and eluted with a gradient of 40%-60% CH$_3$CN in 0.05M (NH$_4$)$_2$SO$_4$, pH 2.5, at 10 ml/min during 50 min at 40° C. The peptide-containing fractions were collected and diluted with H$_2$O and passed through a Sep-Pak® C18 cartridge (Waters part. #:51910) which had been equilibrated with 0.1% TFA. It was then eluted with 70% CH$_3$CN containing 0.1% TFA and the purified peptide was isolated by lyophilisation after dilution of the eluate with water.

The final product obtained was characterised by analytical RP-HPLC (retention time) and by LCMS.

The RP-HPLC analysis was performed using UV detection at 214 nm and a Vydac 218TP54 4.6 mm×250 mm C-18 silica column (The Separations Group, Hesperia, USA) which was eluted at 1 ml/min at 42° C. Two different elution conditions were used:

A1: Equilibration of the column with in a buffer consisting of 0.1M $(NH_4)_2SO_4$, which was adjusted to pH 2.5 with concentrated $H_2SO_4$ and elution by a gradient of 0% to 60% $CH_3CN$ in the same buffer during 50 min.

B1: Equilibration of the column with 0.1% $TFA/H_2O$ and elution by a gradient of 0% $CH_3CN/0.1\%$ $TFA/H2O$ to 60% $CH_3CN/0.1\%$ $TFA/H_2O$ during 50 min.

B6: Equilibration of the column with 0.1% $TFA/H_2O$ and elution by a gradient of 0% $CH_3CN/0.1\%$ $TFA/H2O$ to 90% $CH_3CN/0.1\%$ $TFA/H_2O$ during 50 min.

LCMS was performed on a setup consisting of Hewlett Packard series 1100 G1312A Bin Pump, Hewlett Packard series 1100 Column compartment, Hewlett Packard series 1100 G1315A DAD diode array detector, Hewlett Packard series 1100 MSD and Sedere 75 Evaporative Light Scattering detector controlled by HP Chemstation software. The HPLC pump is connected to two eluent reservoirs containing:

A: 10 mM $NH_4OH$ in water
B: 10 mM $NH_4OH$ in 90% acetonitrile

The analysis was performed at 23° C. by injecting an appropriate volume of the sample (preferably 20 μl) onto the column which is eluted with a gradient of A and B.

WORKING EXAMPLES

Example 1

Propyloxycarbonyl-(4-amidino-Phe)-Glu-Asn-Cha-[HN—$(CH_2$—$CH_2$—$O)_2$—$(CH_2)$—C(═O)$]_5$—$NH_2$

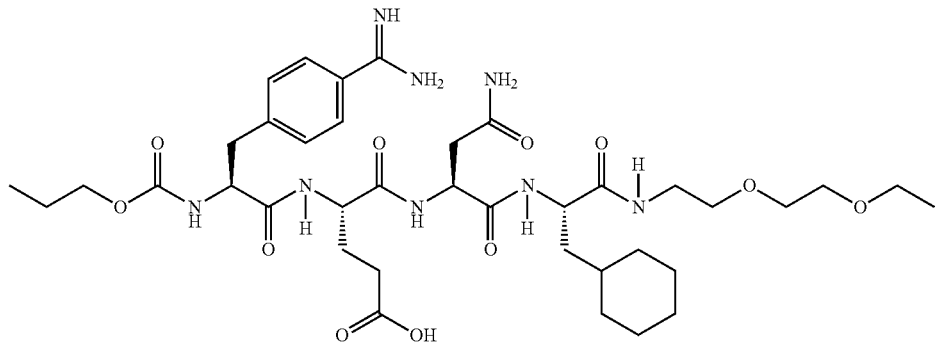

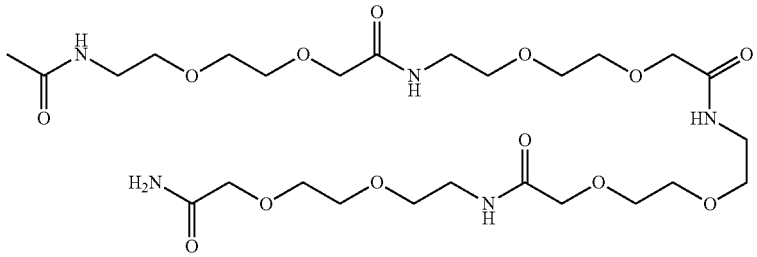

LCMS: ½[M(H+)$_2$]=708.98% pure by ELS.

Example 2

Propyloxycarbonyl-HomoArg-Glu-Asn-Cha-[HN—$(CH_2$—$CH_2$—$O)_2$—$(CH_2)$—C(═O)$]_5$—$NH_2$

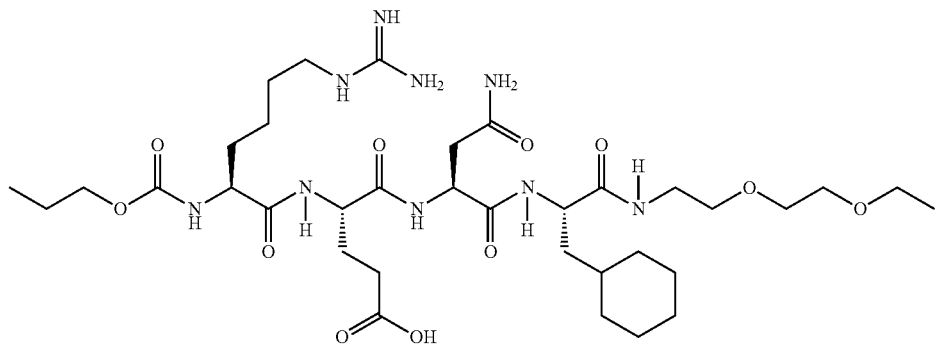

-continued
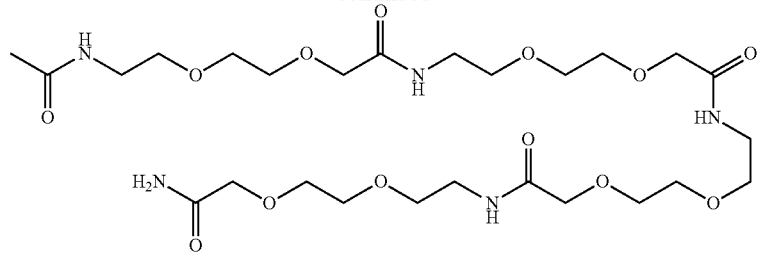
LCMS: MH+=1396. 100% pure by ELS.
Example 3
Propyloxycarbonyl-(4-amidinoPhe)-Glu-Asn-Cha-Arg-Arg-Arg-NH$_2$
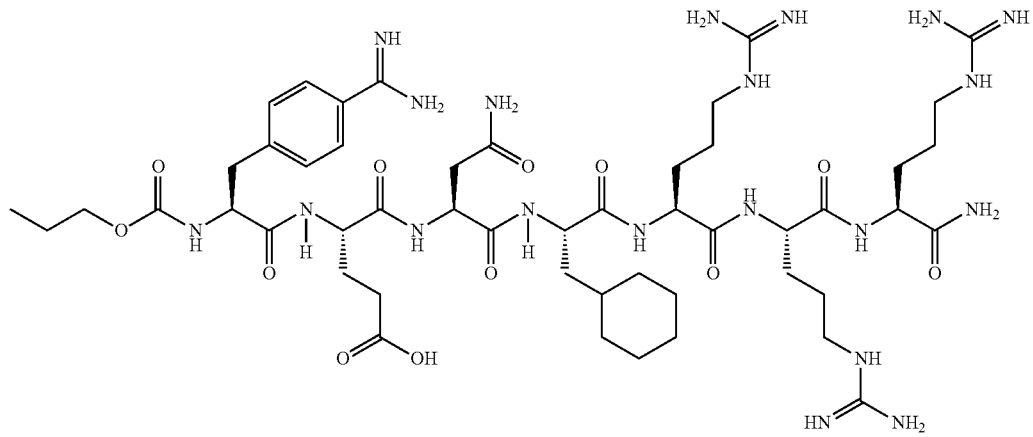 [SMILES: CCCOC(=O)N[C@@H](Cc1ccc(C(=N)N)cc1)C(=O)N[C@@H](CCC(=O)O)C(=O)N[C@@H](CC(N)=O)C(=O)N[C@@H](CC1CCCCC1)C(=O)N[C@@H](CCCNC(=N)N)C(=O)N[C@@H](CCCNC(=N)N)C(=O)N[C@@H](CCCNC(=N)N)C(N)=O]
LCMS: MH+=1157. 91% pure by HPLC (214 nm).
Example 4
Propyloxycarbonyl-(4-amidino-Phe)-Glu-Asn-Cha-[HN—(CH$_2$—CH$_2$—O)$_2$—(CH$_2$)—C(=O)]$_{10}$—NH$_2$
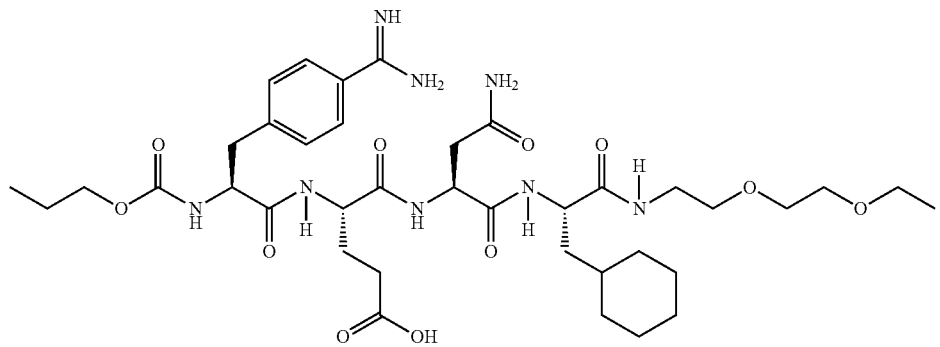

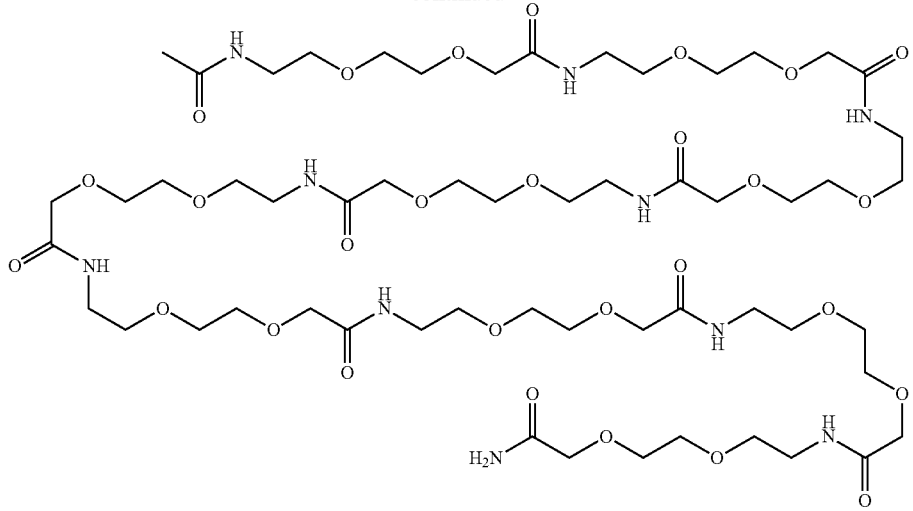

Example 5

Stabilization of Factor VIIa Molecules

In order to investigate the stabilizing effect of the compounds described by the current invention on Factor VIIa molecules in solution, a stability experiment was performed on 40K-PEG-rFVIIa.

The investigated formulations contained 0, 1, 10 or 30 mM n-propyloxycarbonyl-Phe(4-amidino)-Glu-Asn-Cha-(OEG)$_5$-NH2, and all contained 20 mg/ml 40K-PEG-rFVIIa, 20 mM histidine, pH 7.0, 6% sucrose, 20 mM CaCl$_2$, 0.5 mg/ml methionine. The samples were incubated 3 months at 25° C., and analysed for clot activity using the above-described "One-stage Coagulation Assay" (Assay 4) (see section "General Methods").

The following table shows the measured activities relative to the initial values:

| Inhibitor concentration | 0 mM | 1 mM | 10 mM | 30 mM |
|---|---|---|---|---|
| Activity | ~ | 18% | 86% | 89% |

The activity in the sample with 0 mM inhibitor after 3 months was too low to be measured in the assay.

Clearly, the results show a pronounced stabilisation by the presence of the inhibitor, with the largest effect above 1 mM concentration.

---

The invention claimed is:

1. A compound of general formula (I)

$$X^1\text{-}X^2\text{-}X^3\text{-}X^4\text{-}X^5\text{-}(X^6)_n\text{-}(X^7)_m\text{-}Y \quad (I)$$

wherein $X^1$ represents lower alkoxycarbonyl, lower alkenyloxycarbonyl, alkynyloxycarbonyl, cycloalkyloxycarbonyl, cycloalkylalkyloxycarbonyl, aryloxycarbonyl, arylalkyloxycarbonyl, or heteroarylalkyloxycarbonyl, lower alkylaminocarbonyl, lower alkenylaminocarbonyl, alkynylaminocarbonyl, cycloalkylaminocarbonyl, cycloalkylalkylaminocarbonyl, arylaminocarbonyl, arylalkylaminocarbonyl, or heteroarylalkylaminocarbonyl, lower alkanoyl, lower alkenoyl, lower alkadienyl, alkynoyl, cycloalkanoyl, cycloalkylalkanoyl, cycloalkenylalkanoyl, aroyl, arylalkanoyl, or heteroarylalkanoyl, wherein said groups are optionally substituted with halogen, hydroxyl, lower alkyl, lower alkoxy, lower alkylthio, or cyano;

$X^2$ represents 4-amidino-Phe, Arg, HomoArg, Orn, Lys, Dab, or Dap;

$X^3$ represents Glu, Asp, (α-Me)Glu, 1-aminocyclobutane-trans-1,3-dicarboxylic acid, or 1-aminocyclobutane-cis-1,3-dicarboxylic acid;

$X^4$ represents Arg, HomoArg, Lys, His, Asn, Gln, Trp, Phe, Phg, Glu, D-Glu, Asp, D-Asp, Dab, Dap, Nβ-[amidino]-Dap, or Nγ-[amidino]Dab;

$X^5$ represents Phg, D-Phg, Phe, Val, Ile, Leu, Lys, Ala, Glu, Gly, Aib, Trp, Abu, Alle, Cha, Hph, Nle, or Nva;

$X^6$ represents Arg, HomoArg, Lys, Orn, His or Lys(mPeg (1-10k)-CO);

$X^7$ represents a diradical of general formula —HN—$(CH_2$—$CH_2$—$O)_{1-10}$—$(CH_2)_{1-5}$—$C(=O)$—;

Y represents $NH_2$ or OH; and n is 0 or 3-6 and m is 0-20, with the proviso that n and m must not be zero simultaneously, including any and all stereoisomeric form or forms thereof, any mixture of two or more such compounds of formula I in any ratio, and physiologically acceptable salts thereof.

2. The compound according to claim 1, wherein X represents lower alkoxycarbonyl, lower alkenyloxycarbonyl, alkynyloxycarbonyl, cycloalkyloxycarbonyl, cycloalkylalkyloxycarbonyl, lower alkylaminocarbonyl, lower alkenylaminocarbonyl, alkynylaminocarbonyl, cycloalkylaminocarbonyl, cycloalkylalkylaminocarbonyl, lower alkanoyl, lower alkenoyl, alkynoyl, cycloalkanoyl, or cycloalkylalkanoyl, and wherein said groups are optionally substituted with halogen, lower alkyl, lower alkoxy, or lower alkylthio.

3. The compound according to claim 2, wherein X represents methoxycarbonyl, ethoxycarbonyl, propyloxycarbonyl, 2-(methoxy)ethoxycarbonyl, 2-(methylthio)ethoxycarbonyl, isopropoxycarbonyl, allyloxycarbonyl, 2-chloroallyloxycarbonyl, propargyloxycarbonyl, isobutoxycarbonyl, cyclobutyloxycarbonyl, cyclopentyloxycarbonyl, cyclopropylmethyloxycarbonyl, methylaminocarbonyl, dimethylaminocarbonyl, ethylaminocarbonyl, diethylaminocarbonyl, propylaminocarbonyl, isopropylaminocarbonyl, allylaminocarbonyl, cyclobutylaminocarbonyl, cyclopentylaminocarbonyl, cyclopropylmethylaminocarbonyl, acetyl, propionyl, butyryl, pentanoyl, 3-cyclopropylpropionyl, pent-4-enoyl, 2-methyl-4-pentenoyl, 4-hexenoyl, 3-cyclopenten-1-oyl, 4,5,5-trifluoropent-4-enoyl, or hexa-2,4-dienoyl.

4. The compound according to claim 3, wherein $X^1$ represents propyloxycarbonyl.

5. The compound according to claim 1, wherein $X^2$ represents 4-amidino-Phe, Arg, HomoArg, Orn, or Lys.

6. The compound according to claim 5, wherein $X^2$ represents 4-amidino-Phe.

7. The compound according to claim 1, wherein $X^3$ represents Glu.

8. The compound according to claim 1, wherein $X^4$ represents Arg, HomoArg, Lys, His, Asn, Gln, Dab, or Dap.

9. The compound according to claim 8, wherein $X^4$ represents Asn or Gln.

10. The compound according to claim 1, wherein $X^5$ represents Phe, Val, Ile, Leu, Ala, Cha, Gly, or Trp.

11. The compound according to claim 10, wherein $X^5$ represents Phe, Cha, or Trp.

12. The compound according to claim 1, wherein $X^6$ represents His, Arg, HomoArg, or Orn.

13. The compound according to claim 12, wherein $X^6$ represents Arg.

14. The compound according to claim 1, wherein $X^7$ represents —HN—$(CH_2$—$CH_2$—$O)_2$—$(CH_2)$—$C(=O)$— or —HN—$(CH_2$—$CH_2$—$O)_2$—$(CH_2)_3$—$C(=O)$—.

15. The compound according to claim 1, wherein n is 3-6 and m is 0.

16. The compound according to claim 15, wherein n is 3 and m is 0.

17. The compound according to claim 1, wherein n is 0 and m is 1-20.

18. The compound according to claim 17, wherein n is 0 and m is 5.

19. The compound according to claim 17, wherein n is 0 and m is 10.

20. The compound according to claim 1, wherein the compound is selected from the list of:

Propyloxycarbonyl-(4-amidino-Phe)-Glu-Asn-Cha-[HN—$(CH_2$—$CH_2$—$O)_2$—$(CH_2)$—$C(=O)]_5$—$NH_2$;

Propyloxycarbonyl-(4-amidino-Phe)-Glu-Asn-Cha-[HN—$(CH_2$—$CH_2$—$O)_2$—$(CH_2)$—$C(=O)]_{10}$—$NH_2$;

Propyloxycarbonyl-(4-amidino-Phe)-Glu-Asn-Cha-$[Arg]_3$—$NH_2$;

Propyloxycarbonyl-HomoArg-Glu-Asn-Cha-[HN—$(CH_2$—$CH_2$—$O)_2$—$(CH_2)$—$C(=O)]_5$—$NH_2$;

Propyloxycarbonyl-HomoArg-Glu-Asn-Cha-[HN—$(CH_2$—$CH_2$—$O)_2$—$(CH_2)$—$C(=O)]_{10}$—$NH_2$;

Propyloxycarbonyl-HomoArg-Glu-Asn-Cha-$[Arg]_3$—$NH_2$, including any and all stereoisomeric form or forms thereof, any mixture of two or more such compounds of formula I in any ratio, and physiologically acceptable salts thereof.

21. A pharmaceutical composition, comprising: one or more compounds according to claim 1, or physiologically acceptable salts thereof; and a Factor VII polypeptide.

22. The pharmaceutical composition according to claim 21, wherein said Factor VII polypeptide is wild-type human Factor VIIa.

23. The pharmaceutical composition according to claim 21, wherein said Factor VII polypeptide is a PEGylated Factor VII.

24. The pharmaceutical composition according to claim 21, further comprising a pharmaceutically acceptable carrier or diluent.

25. The pharmaceutical composition according to claim 21, which is a liquid, aqueous composition.

26. A method of preparing a composition, comprising a Factor VII polypeptide, comprising: adding a compound according to claim 1, or a physiologically acceptable salt thereof, to a sample containing said Factor VII polypeptide; or adding said Factor VII polypeptide to a sample containing a compound according to claim 1, or a physiologically acceptable salt thereof.

27. The method according to claim 26, wherein said Factor VII polypeptide is wild-type human Factor VIIa.

28. The method according to claim 26, wherein said Factor VII polypeptide is a PEGylated Factor VII.

29. The method according to claim 26, wherein said compound or salt thereof and/or said Factor VII polypeptide is present in a liquid, aqueous medium.

30. The pharmaceutical composition prepared by a method according to claim 26.

31. A method of inhibiting a Factor VII polypeptide, comprising: adding a compound according to claim 1, or a physiologically acceptable salt thereof, to a sample containing said Factor VII polypeptide; or adding said Factor VII polypeptide to a sample containing a compound according to claim 1, or a physiologically acceptable salt thereof.

32. The method according to claim 31, wherein said Factor VII polypeptide is wild-type human Factor VIIa.

33. The method according to claim 31, wherein said Factor VII polypeptide is a PEGylated Factor VII.

34. The method according to claim 31, wherein said compound or salt thereof and/or said Factor VII polypeptide is present in a liquid, aqueous medium.

* * * * *

UNITED STATES PATENT AND TRADEMARK OFFICE
CERTIFICATE OF CORRECTION

PATENT NO.         : 8,486,892 B2
APPLICATION NO.    : 12/811854
DATED              : July 16, 2013
INVENTOR(S)        : Florencio Z. Dorwald It is certified that error appears in the above-identified patent and that said Letters Patent is hereby corrected as shown below:

In the Claims:

At column 36, claim number 1, line number 65, please delete "H is" and insert therefore --His--.

At column 37, claim number 8, line number 3, please delete "H is" and insert therefore --His--.

At column 37, claim number 8, line number 47, please delete "H is" and insert therefore --His--.

At column 37, claim number 12, line number 55, please delete "H is" and insert therefore --His--.

Signed and Sealed this
Twelfth Day of November, 2013

Teresa Stanek Rea
*Deputy Director of the United States Patent and Trademark Office*

SEQUENCE LISTING

```
<160> NUMBER OF SEQ ID NOS: 4

<210> SEQ ID NO 1
<211> LENGTH: 4
<212> TYPE: PRT
<213> ORGANISM: Artificial
<220> FEATURE:
<223> OTHER INFORMATION: FVII inhibitor:
      Propyloxycarbonyl-(4-amidino-Phe)-Glu-Asn-Cha-[HN-(CH2-CH2-O)2-
      (CH2)-C(=O)]5-NH2;
<220> FEATURE:
<221> NAME/KEY: MISC_FEATURE
<222> LOCATION: (1)..(1)
<223> OTHER INFORMATION: 4-amidino-Phe, 4-amidino-phenylalanine
<220> FEATURE:
<221> NAME/KEY: MISC_FEATURE
<222> LOCATION: (4)..(4)
<223> OTHER INFORMATION: Cha, beta-cyclohexylalanine

<400> SEQUENCE: 1

Xaa Glu Asn Xaa
1

<210> SEQ ID NO 2
<211> LENGTH: 7
<212> TYPE: PRT
<213> ORGANISM: Artificial
```

```
<220> FEATURE:
<223> OTHER INFORMATION: FVII inhibitor:
      Propyloxycarbonyl-(4-amidino-Phe)-Glu-Asn-Cha-[Arg]3-NH2;
<220> FEATURE:
<221> NAME/KEY: MISC_FEATURE
<222> LOCATION: (1)..(1)
<223> OTHER INFORMATION: 4-amidino-Phe, 4-amidino-phenylalanine
<220> FEATURE:
<221> NAME/KEY: MISC_FEATURE
<222> LOCATION: (4)..(4)
<223> OTHER INFORMATION: Cha, beta-cyclohexylalanine

<400> SEQUENCE: 2

Xaa Glu Asn Xaa Arg Arg Arg
1               5

<210> SEQ ID NO 3
<211> LENGTH: 4
<212> TYPE: PRT
<213> ORGANISM: Artificial
<220> FEATURE:
<223> OTHER INFORMATION: FVII inhibitor:
      Propyloxycarbonyl-HomoArg-Glu-Asn-Cha-[HN-(CH2-CH2-O)2-(CH2)-
      C(=O)]5-NH2;
<220> FEATURE:
<221> NAME/KEY: MISC_FEATURE
<222> LOCATION: (1)..(1)
<223> OTHER INFORMATION: homoArg, homo-arginine, N-epsilon-amidinolysine
<220> FEATURE:
<221> NAME/KEY: MISC_FEATURE
<222> LOCATION: (4)..(4)
<223> OTHER INFORMATION: Cha, beta-cyclohexylalanine

<400> SEQUENCE: 3

Xaa Glu Asn Xaa
1

<210> SEQ ID NO 4
<211> LENGTH: 7
<212> TYPE: PRT
<213> ORGANISM: Artificial
<220> FEATURE:
<223> OTHER INFORMATION: FVII inhibitor: Propyloxycarbonyl-HomoArg-Glu-
      Asn-Cha-[Arg]3-NH2,
<220> FEATURE:
<221> NAME/KEY: MISC_FEATURE
<222> LOCATION: (1)..(1)
<223> OTHER INFORMATION: homoArg, homo-arginine, N-epsilon-amidinolysine
<220> FEATURE:
<221> NAME/KEY: MISC_FEATURE
<222> LOCATION: (4)..(4)
<223> OTHER INFORMATION: Cha, beta-cyclohexylalanine

<400> SEQUENCE: 4

Xaa Glu Asn Xaa Arg Arg Arg
1               5
```